US012702133B2

(12) United States Patent
Desai et al.

(10) Patent No.: US 12,702,133 B2
(45) Date of Patent: Aug. 11, 2026

(54) AGROCHEMICAL COMPOSITION

(71) Applicant: UPL Limited, Mumbai (IN)

(72) Inventors: Sujata Dhondiram Desai, Mumbai (IN); Prakash Mahadeo Jadhav, Lawrence Township, NJ (US)

(73) Assignee: UPL LTD, Mumbai (IN)

(*) Notice: Subject to any disclaimer, the term of this patent is extended or adjusted under 35 U.S.C. 154(b) by 826 days.

(21) Appl. No.: 17/912,113

(22) PCT Filed: Mar. 19, 2021

(86) PCT No.: PCT/IB2021/052316

§ 371 (c)(1),
(2) Date: Sep. 16, 2022

(87) PCT Pub. No.: WO2021/186406

PCT Pub. Date: Sep. 23, 2021

(65) Prior Publication Data

US 2023/0133320 A1 May 4, 2023

(30) Foreign Application Priority Data

Mar. 20, 2020 (IN) ............................. 202021012142

(51) Int. Cl.

| | |
|---|---|
| ***A01N 43/707*** | (2006.01) |
| ***A01N 25/04*** | (2006.01) |
| ***A01N 25/12*** | (2006.01) |
| ***A01N 43/653*** | (2006.01) |
| ***A01P 13/00*** | (2006.01) |
| ***C07D 249/12*** | (2006.01) |
| ***C07D 253/06*** | (2006.01) |
| ***C07D 253/075*** | (2006.01) |

(52) U.S. Cl.

CPC ........... *A01N 43/707* (2013.01); *A01N 25/04* (2013.01); *A01N 25/12* (2013.01); *A01N 43/653* (2013.01); *A01P 13/00* (2021.08); *C07D 249/12* (2013.01); *C07D 253/06* (2013.01); *C07D 253/075* (2013.01)

(58) Field of Classification Search

CPC .... A01N 43/707; A01N 43/653; A01N 25/04; A01N 25/12; A01P 13/00; C07D 249/12; C07D 253/075; C07D 253/06

See application file for complete search history.

(56) References Cited

U.S. PATENT DOCUMENTS

| | | | |
|---|---|---|---|
| 3,905,801 | A | 9/1975 | Fawzi |
| 4,818,275 | A | 4/1989 | Theodoridis |
| 2003/0148887 | A1 | 8/2003 | Bratz et al. |
| 2019/0337905 | A1 | 11/2019 | Nicholson et al. |

FOREIGN PATENT DOCUMENTS

| | | | |
|---|---|---|---|
| CN | 104115842 | A | 10/2014 |
| WO | 2017197909 | A1 | 11/2017 |
| WO | 2019123186 | A1 | 6/2019 |
| WO | 2019186299 | A1 | 10/2019 |

OTHER PUBLICATIONS

CN104115842A, Weeding composition containing sulfentrazone and metribuzin and application thereof, 2014, Description, English translation powered by EPO and Google, 10 pages. (Year: 2014).*

Chopra, D. et al.; "Exploring polymorphism by solvent mediation in potentially active herbicideMetribuzin: A subtle interplay of weak intermolecular interactions"; CrystEngComm, vol. 7; 2005; pp. 374-379; DOI: https://doi.org/10.1039/B504347F.

International Search Report and Written Opinion for International Application PCT/IB2021/052316; International Filing Date: Mar. 19, 2021; Date of Mailing: May 24, 2021; 11 pages.

* cited by examiner

*Primary Examiner* — Ali Soroush
*Assistant Examiner* — Andriae M Holt
(74) *Attorney, Agent, or Firm* — CANTOR COLBURN LLP

(57) ABSTRACT

The present invention provides a co-crystal of sulfentrazone and a triazinone herbicide and process for preparation thereof. The present invention also provides an agrochemical composition comprising said co-crystal and process of preparation of an agrochemical composition and method of controlling weeds with said compositions.

15 Claims, 7 Drawing Sheets

DAD: Signal A, 240.0 nm/Bw:4.0 nm Ref 360.0 nm/Bw:100.0 nm

RESULTS

| NAME | RETENTION TIME | AREA | AREA % |
|---|---|---|---|
| METRIBUZINE | 11.520 | 581810669 | 52.36 |
| SULFENTRAZONE | 12.473 | 529260711 | 47.64 |

| TOTALS | | | |
|---|---|---|---|
| | | 1111071380 | 100.00 |

| SOURCE SPECTRA RESULTS | |
|---|---|
| SPECTRUM NAME | NUMBER OF PEAKS |
| SULFENTRAZONE-METRIBUZINE SC#509 7959 | |

AGROCHEMICAL COMPOSITION

CROSS REFERENCE TO RELATED APPLICATIONS

This application is a National Stage application of PCT/IB2021/052316, filed Mar. 19, 2021, which claims priority to Indian Patent Application number 202021012142, filed Mar. 20, 2020, both of which are incorporated by reference in their entirety herein.

FIELD OF THE INVENTION

The present invention relates to an agrochemical composition. The present invention more particularly relates to an agrochemical composition comprising co-crystal of sulfentrazone and triazinone herbicide.

BACKGROUND OF THE INVENTION

Co-crystals are multi-component crystalline systems formed by intermolecular interactions without transfer of hydrogen ions. Co-crystals of organic compounds, or crystalline complexes, are multi-component systems which comprise at least two different organic compounds. Co-crystallization is a manifestation of directed self-assembly of different components.

An agrochemical co-crystal can be defined as crystalline materials comprised of two or more different active ingredients or with one or more actives with other co-formers. These compounds can be formed by intermolecular forces such as hydrogen bonding, π-stacking and van der Waal's forces. Co-crystals may alter or enhance several important physico-chemical characteristics of the substances like solubility, bioavailability, stability, hygroscopicity, surface free energy, zeta potential, crystal hardness, filterability, filtration and flow ability. These properties have a significant influence on agrochemical formulation.

The use of agrochemical composition is a widespread and documented practice in the agricultural community. These agrochemical composition offer significant advantages over individual applications including improved and extended control, reduced application rates and costs, shorter contact times for improved results, less stringent use restrictions, improved selectivity, improved spectrum for fungi, insects, weeds etc. which are controlled, and reduced residue problems.

However, the combined use of a plurality of active substances sometimes lead to phenomena of a physical and biological incompatibility, for example lacking physical stability of a coformulation, decomposition of an active substance or antagonism of the active substances and therefore are to be tackled carefully.

Triazinone is a heterocyclic compound with potential biological activity. Their principal mode of action is an inhibition of the electron transport in photosystem II (Hill reaction).

Sulfentrazone is a phenyl triazinone (also termed as aryl triazinone) herbicides that acts by inhibiting protoporphyrinogen oxidase (protox). Sulfentrazone mimic half of the tetrapyrrole ring of protoporphyrinogen (the substrate of Protox) and compete for the catalytic site on the enzyme. The active compound sulfentrazone is also known for a long time (U.S. Pat. No. 4,818,275) and is absorbed by the roots and foliage, with translocation primarily in the apoplasm, and limited movement in the phloem. It is used to control annual broad-leaved weeds, some grasses and *Cyperus* spp. in soya beans, sugar cane and tobacco. Applied as pre-emergence or pre-plant incorporation. Metribuzin is a triazinone herbicide that inhibits photosynthesis in a susceptible plant by binding to a protein of the photosystem II complex, which in turn, cause a chain of events where, eventually, plant lipids and proteins are attacked and oxidized by highly reactive free radicals. The active compound metribuzin has been known for a long time (U.S. Pat. No. 3,905,801) and is used both as pre- and post-emergence and has proved useful for the selective control of weeds, in particular in soybean and potato.

It has been observed that while making a stable composition, especially the liquid composition of sulfentrazone and triazinone herbicide (e.g. metribuzin), physical incompatibility of these two active leads to an unstable composition. Such unstable composition is unacceptable from formulation part as well as application part. During formulation, such liquid composition may not pass quality check due to non-uniform dispersion. And, during application, such liquid composition may not deliver uniform concentration of actives in the field and may cause nozzle choking of applicators. Therefore, need exist to develop a stable system wherein sulfentrazone can be formulated with other triazinone herbicides as binary mixture. Also, need exist to develop a stable system wherein sulfentrazone and triazinone herbicides when formulated together, doesn't show crystal growth and remain stable during formulation and upon storage.

OBJECT OF THE INVENTION

It is an object of the present invention to provide a co-crystal of sulfentrazone and a triazinone herbicide.

It is another object of the present invention to provide an agrochemical composition of sulfentrazone and triazinone herbicide.

It is an object of the present invention to provide an agrochemical composition of sulfentrazone and triazinone herbicide with long term storage stability.

It is another object of the present invention to provide an agrochemical composition comprising a co-crystal of sulfentrazone and triazinone herbicide.

It is another object of the present invention to provide an agrochemical composition comprising a co-crystal of sulfentrazone and metribuzin.

It is another object of the present invention to provide a process for preparing agrochemical composition comprising a co-crystal of sulfentrazone and triazinone herbicide.

SUMMARY OF THE INVENTION

In an aspect of the present invention provides a co-crystal of sulfentrazone and a triazinone herbicide.

In another aspect the present invention provides a process for preparation of a co-crystal of sulfentrazone and a triazinone herbicide.

In another aspect, the present invention provides an agrochemical composition comprises of a co-crystal of sulfentrazone and a triazinone herbicide.

In another aspect, the present invention provides a process for preparation of an agrochemical composition comprises co-crystal of sulfentrazone and a triazinone herbicide.

In another aspect of the present invention, a process for preparing an agrochemical composition comprising cocrystal of sulfentrazone and a triazinone herbicide said process comprising:

a) pre-treatment to sulfentrazone and a triazinone herbicide to form a co-crystal;
b) admixing co-crystal of step (a) with agrochemical excipients as required to obtain mixture; and
c) further processing the resulting mixture of step (b) to obtain said composition.

In an aspect of the present invention, a process for preparing a liquid agrochemical composition comprising co-crystal of sulfentrazone and a triazinone herbicide said process comprising:

a) pre-treatment to sulfentrazone and a triazinone herbicide to form a co-crystal;
b) admixing co-crystal of step (a) with agrochemical excipients as required in an aqueous condition to obtain mixture; and
c) further processing the resulting mixture of step (b) to obtain said composition In yet another aspect of the present invention, an agrochemical composition comprises a co-crystal of sulfentrazone and metribuzin.

In another aspect of the present invention, an agrochemical composition comprising a co-crystal of sulfentrazone and metribuzin wherein said composition comprises between 10-90% of sulfentrazone and 90-10% of metribuzin by weight.

In another aspect of the present invention, an agrochemical composition comprising a co-crystal of sulfentrazone and metribuzin wherein the co-crystal exhibits at least one of the characteristic-XRD reflexes at 2θ values (±0.2) of 7.8°, 11.8°, 14.1°, 17.8°, 22.1°, 23.4° and 24.4°.

In an aspect of the present invention, a co-crystal of sulfentrazone and metribuzin is provided.

In another aspect of the present invention, a process for preparing a co-crystal of sulfentrazone and metribuzin by using any of the following methods:

i. solution crystallization,
ii. dry grinding,
iii. solvent drop grinding technique,
iv. melt crystallization, or
v. mixing sulfentrazone and a triazinone herbicide in an aqueous condition followed by providing energy.

In yet another aspect of the present invention, a process for preparing an agrochemical composition comprising cocrystal of sulfentrazone and metribuzin said process comprising:

a) pre-treatment to sulfentrazone and metribuzin to form a co-crystal;
b) admixing co-crystal of step (a) with agrochemical excipients as required to obtain mixture; and
c) further processing the resulting mixture of step (b) to obtain said composition In another aspect of the present invention, a process for preparing a liquid agrochemical composition comprising co-crystal of sulfentrazone and metribuzin said process comprising:

(a) pre-treatment to sulfentrazone and metribuzin to form a co-crystal;
(b) admixing co-crystal of step (a) with agrochemical excipients in an aqueous condition to obtain said composition In another aspect of the present invention, a method of controlling weeds said method comprising applying to a plant, or its habitat, plant seed or soil, a herbicidally effective amount of a composition comprising a co-crystal of sulfentrazone and a triazinone herbicide.

In another aspect of the present invention, a method of controlling weeds said method comprising applying to a plant, or its habitat, plant seed or soil, a herbicidally effective amount of a composition comprising a co-crystal of sulfentrazone and metribuzin. Another aspect of the present invention provides use of liquid agrochemical composition comprising co-crystal of sulfentrazone and a triazinone herbicide.

BRIEF DESCRIPTION OF THE DRAWINGS

The present invention can be understood by reference to the following figures.

DETAILED DESCRIPTION OF THE INVENTION

Figure 1:
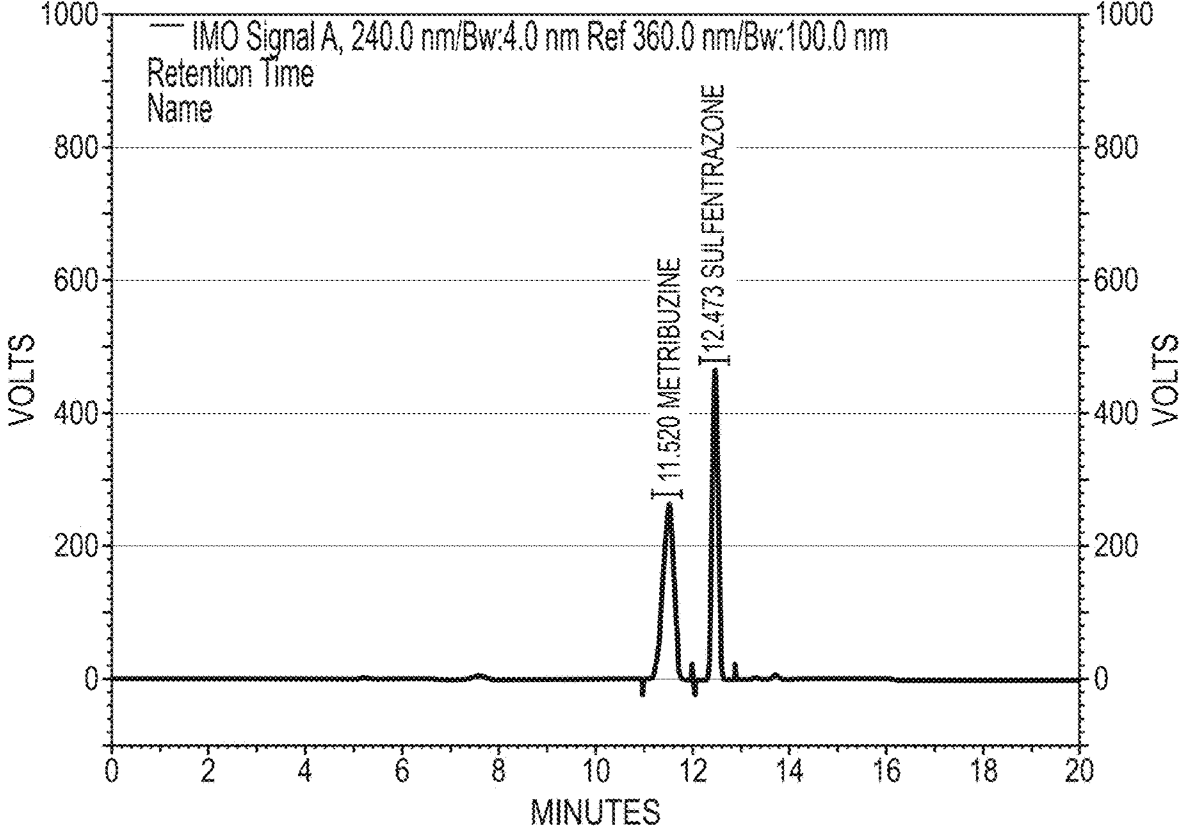
FIG. 1: High Performance Liquid Chromatography (HPLC) chromatogram of co-crystal of sulfentrazone and metribuzin.

Surprisingly, inventors of the present invention found that an agrochemical composition of sulfentrazone and metribuzin can be formed when both the actives are allowed for pre-treatment that include interaction of two actives and further formulating using surfactants and other agrochemical excipients. Such pre-treatment facilitates intermolecular interaction between said actives and leads to the formation of a co-crystal of two actives. And, then such pre-formed co-crystal can be formulated into desired products using surfactants and other agrochemical excipients. Further it has been observed by the inventors of the present invention that when said agrochemical composition is formulated as liquid compositions comprising a co-crystal of sulfentrazone and triazinone herbicide, it does not suffer from particle growth issues associated with liquid compositions and further noted that said compositions remain quite stable during longtime storage.

In the context of the present invention the term 'co-crystals' is defined as "solids that are crystalline materials composed of two or more molecules in the same crystal lattice". Co-crystal is also defined as crystalline materials composed of two or more different molecules, in a defined stoichiometric ratio within the same crystal lattice and are associated by nonionic and noncovalent bonds.

Thus, in an embodiment, the present invention provides an agrochemical composition comprising a co-crystal of sulfentrazone and a triazinone herbicide.

In an embodiment of the present invention, there is provided an agrochemical composition comprising a co-crystal of sulfentrazone and a triazinone herbicide wherein said composition comprises between 10-90% of sulfentrazone and 90-10% of triazinone herbicide by weight.

In an embodiment of the present invention, triazinone herbicide of the agrochemical composition is selected from the group comprising of ametridione, amibuzin, ethiozin, hexazinone, isomethiozin, metamitron, metribuzin and trifludimoxazin.

In an embodiment of the present invention, triazinone herbicide is metamitron.

In an embodiment of the present invention, triazinone herbicide amibuzin.

In a preferred embodiment of the present invention, triazinone herbicide is metribuzin.

In an embodiment of the present invention, sulfentrazone of the agrochemical composition comprising a co-crystal of sulfentrazone and a triazinone herbicide is from about 10% w/w to about 90% w/w sulfentrazone of the total weight of the agrochemical composition.

In an embodiment of the present invention, sulfentrazone of the agrochemical composition comprising a co-crystal of sulfentrazone and a triazinone herbicide is from about 20% w/w to about 80% w/w sulfentrazone and preferably, from about 40% w/w to about 60% w/w sulfentrazone of the total weight of the agrochemical composition. In an embodiment of the present invention, triazinone herbicide of the agrochemical composition comprising a co-crystal of sulfentrazone and triazinone herbicide is from about 10% w/w to about 90% w/w triazinone herbicide of the total weight of the agrochemical composition.

In an embodiment of the present invention, triazinone herbicide of the agrochemical composition comprising a co-crystal of sulfentrazone and triazinone herbicide is from about 20% w/w to about 80% w/w triazinone herbicide and preferably, from about 40% w/w to about 60% w/w triazinone herbicide of the total weight of the agrochemical composition.

According to an embodiment of the present invention, a process for preparing an agrochemical composition comprising co-crystal of sulfentrazone and a triazinone herbicide is provided wherein, said process comprising steps of:

a) pre-treatment to sulfentrazone and a triazinone herbicide to form a co-crystal;
b) admixing co-crystal of step (a) with agrochemical excipients as required to obtain mixture; and
c) further processing the resulting mixture of step (b) to obtain said composition As used herein after, the term "pre-treatment" refers to the process of allowing sulfentrazone and a triazinone herbicide to form a co-crystal prior to its incorporation in the agrochemical composition.

In an embodiment of the present invention, pre-treatment comprises milling, grinding or providing suitable form of energy sufficient to allow the formation of co-crystal of sulfentrazone and triazinone herbicide.

In an embodiment of the present invention, pre-treatment comprises heating the mixture of sulfentrazone and triazinone herbicide and allowing the formation of co-crystal of sulfentrazone and triazinone herbicide.

In an embodiment of the present invention, pre-treatment comprises subjecting the mixture of sulfentrazone and triazinone herbicide to amorphization by way of grinding, melting, milling or other suitable means and allowing the formation of co-crystal of sulfentrazone and triazinone herbicide.

In an embodiment of the present invention pre-treatment is provided for sulfentrazone and a triazinone herbicide for an adequate time period to form the co-crystal.

According to another embodiment of the present invention, in the process for preparing an agrochemical composition comprising co-crystal of sulfentrazone and a triazinone herbicide, the sequence of mixing co-crystal with agrochemical excipients is not fixed and may vary according to the preference of the formulator.

According to another embodiment of the present invention, in the process for preparing an agrochemical composition comprising co-crystal of sulfentrazone and a triazinone herbicide, the mixture obtained in step (b) is subjected to particle size reduction by applying shear to the mixture of co-crystals and agrochemical excipients. Suitable devices for this purpose are the devices that offers milling operation e.g. high shear mixers like ROSS HSM, Ultra-Turrax apparatus, and dissolvers, static mixers, e.g. systems having mixing nozzles, bead mills, vibratory mills, agitator bead mills, colloid mills, cone mills, circulating mills (agitator ball mills with pin grinding system), disk mills, annular chamber mills, double cone mills, sprocket dispersers or homogenizers and other homogenizers.

According to another embodiment of the present invention, in the process for preparing an agrochemical composition comprising co-crystal of sulfentrazone and a triazinone herbicide, further processing at step (c) can be performed at ambient temperature conditions.

According to another embodiment of the present invention, in the process for preparing an agrochemical composition comprising co-crystal of sulfentrazone and a triazinone herbicide, further processing at step (c) can be performed at an elevated temperature conditions with temperature ≥40° C., preferably ≥60° C.

According to another embodiment of the present invention, in the process for preparing an agrochemical composition comprising co-crystal of sulfentrazone and a triazinone herbicide, further processing at step (c) can be performed in low temperature conditions with temperature ≤40° C., preferably ≤20° C.

According to another embodiment of the present invention, an agrochemical composition of the present invention may be formulated as granular as well as liquid compositions.

In an embodiment there is provided a process for preparing a granular composition comprising a co-crystal of sulfentrazone and a triazinone herbicide.

In an embodiment of the present invention, granular composition comprising a co-crystal of sulfentrazone and a triazinone herbicide is prepared by a process comprising:

a) pre-treatment to sulfentrazone and a triazinone herbicide to form a co-crystal;
b) admixing co-crystal of step (a) with agrochemical excipients as required to mixture;
c) optionally grinding and pulverizing; and further granulating said mixture to obtain granular composition.

The step of granulating the mixture is not particularly limiting. Appropriate granulating processes are conventional processes described in granulating technology for example spray drying, fluidized bed granulation, agglomeration, pan granulation and extrusion granulation.

In an embodiment of the present invention, an agrochemical composition comprising from about 10% to about 40% w/w co-crystal of sulfentrazone and metribuzin, from about 1% to about 20% solvent, from about 0.1% to about 20% non-ionic and anionic dispersing agents, from about 01. % to about 10% wetting agent, from about 0.1% to about 10% defoamer, from about 0.1% to about 30% thickener of the total weight of the agrochemical composition.

In an embodiment of the present invention, an agrochemical composition comprising from about 10% to about 40% w/w co-crystal of sulfentrazone and metribuzin, from about 1% to about 20% diol, from about 0.1% to about 20% acrylic polymer, from about 0.1% to about 20% alkali swellable polyacrylate, from about 0.1% to about 10% polyalkylene glycol ether, from about 0.1% to about 10% silicone defoamer, from about 0.1% to about 30% thickener of the total weight of the agrochemical composition.

The present invention relates to process for preparing a liquid agrochemical composition comprising co-crystal of sulfentrazone and a triazinone herbicide said process comprising:

(a) providing pre-treatment to sulfentrazone and a triazinone herbicide to form a co-crystal;
(b) admixing co-crystal of step (a) with agrochemical excipients as required in an aqueous condition to obtain mixture; and
(c) further processing the resulting mixture of step (b) to obtain said composition In an embodiment of the present invention, pre-treatment comprises milling, grinding or providing suitable form of energy sufficient to allow the formation of co-crystal of sulfentrazone and triazinone herbicide.

In an embodiment of the present invention, pre-treatment comprises heating the mixture of sulfentrazone and triazinone herbicide in aqueous conditions and allowing the formation of co-crystal of sulfentrazone and triazinone herbicide.

In an embodiment of the present invention, pre-treatment comprises subjecting the mixture of sulfentrazone and triazinone herbicide in aqueous conditions to amorphization by way of grinding, melting, milling or other suitable means and allowing the formation of co-crystal of sulfentrazone and triazinone herbicide.

In an embodiment of the present invention, admixing of step b) is performed in aqueous conditions.

In an embodiment of the present invention, processing of step c) is performed in aqueous conditions to obtain the desired product.

The preferred methods for performing step b) and step c) are described previously.

In an embodiment of the present invention, an agrochemical composition comprising a co-crystal of sulfentrazone and metribuzin.

In an embodiment of the present invention, an agrochemical composition comprising a co-crystal of sulfentrazone and metribuzin wherein said composition comprises between 10-90% of sulfentrazone and 90-10% of metribuzin by weight.

In an embodiment of the present invention, sulfentrazone in the agrochemical composition comprising a co-crystal of sulfentrazone and metribuzin is from about 20% w/w to about 80% w/w sulfentrazone and preferably, from about 40% w/w to about 60% w/w sulfentrazone of the total weight of the agrochemical composition.

In an embodiment of the present invention, metribuzin in the agrochemical composition comprising a co-crystal of sulfentrazone and metribuzin is from about 20% w/w to about 80% w/w metribuzin and preferably, from about 40% w/w to about 60% w/w metribuzin of the total weight of the agrochemical composition.

In an embodiment of the present invention, an agrochemical composition comprising a co-crystal of sulfentrazone and metribuzin wherein the co-crystal exhibits at least one of the characteristic-XRD reflexes at 2θ values (±0.2) of 7.8°, 11.8°, 14.1°, 17.8°, 22.1°, 23.4° and 24.4°.

In an embodiment of the present invention, an agrochemical composition comprising from about 10% to about 40% w/w co-crystal of sulfentrazone and metribuzin, from about 1% to about 20% solvent, from about 0.1% to about 20% non-ionic and anionic dispersing agents, from about 01. % to about 10% wetting agent, from about 0.1% to about 10% defoamer, from about 0.1% to about 30% thickener of the total weight of the agrochemical composition wherein said agrochemical composition is formulated as suspension concentrate.

In an embodiment of the present invention, an agrochemical composition comprising from about 10% to about 40% w/w co-crystal of sulfentrazone and metribuzin, from about 1% to about 20% diol, from about 0.1% to about 20% acrylic polymer, from about 0.1% to about 20% alkali swellable polyacrylate, from about 01. % to about 10% polyalkylene glycol ether, from about 0.1% to about 10% silicone defoamer, from about 0.1% to about 30% xanthan gum of the total weight of the agrochemical composition wherein said agrochemical composition is formulated as suspension concentrate.

In an embodiment of the present invention, an agrochemical composition comprising a co-crystal of sulfentrazone and metribuzin wherein the co-crystal exhibits at least one of the characteristic-XRD reflexes at 2 θ values (±0.2) of 7.8°, 11.8°, 14.1°, 17.8°, 22.1°, 23.4° and 24.4°.

In an embodiment of the present invention, an agrochemical composition comprising a co-crystal of sulfentrazone and metribuzin, the molar ratio of sulfentrazone and metribuzin is 1:9 to 9:1.

In an embodiment of the present invention, an agrochemical composition comprising a co-crystal of sulfentrazone and metribuzin, the molar ratio of sulfentrazone and metribuzin is 1:5 to 5:1.

In an embodiment of the present invention, an agrochemical composition comprising a co-crystal of sulfentrazone and metribuzin, the molar ratio of sulfentrazone and metribuzin is generally in the range from 2:1 to 1:2, preferably from 1.5:1 to 1:1.5, and in particular from 1:1.

In an embodiment of the present invention, an agrochemical composition comprising a co-crystal of sulfentrazone and metribuzin, the molar ratio of sulfentrazone and metribuzin is 1:9 to 9:1.

In an embodiment of the present invention, an agrochemical composition comprising a co-crystal of sulfentrazone and metribuzin, the molar ratio of sulfentrazone and metribuzin is generally in the range from 2:1 to 1:2, preferably from 1.5:1 to 1:1.5, and in particular from 1:1.

In an aspect the present invention provides a co-crystal comprising sulfentrazone and at least one triazinone herbicide.

In an embodiment of the present invention, a co-crystal of sulfentrazone and metribuzin is provided.

In an embodiment the sulfentrazone and metribuzin are present in co-crystal in a molar ratio from 2:1 to 1:2.

In an embodiment of the present invention, a co-crystal of sulfentrazone and metribuzin wherein the co-crystal exhibits at least one of the characteristic-XRD reflexes at 2 θ values (±0.2) of 7.8°, 11.8°, 14.1°, 17.8°, 22.1°, 23.4° and 24.4°.

In an embodiment the co-crystal is characterized by at least one of following i. a powder X-ray diffraction pattern comprising at least one peaks at a diffraction angle of 2θ values, 7.8°, 11.8°, 14.1°, 17.8°, 22.1°, 23.4° and 24.4° (±0.2) or
ii. a DSC thermogram comprising an endothermic peak with onset at 107.3° C. and a peak at 110.5° C. or
iii. a single crystal X-ray diffraction having lattice parameters: a=22.2825(4) Å, b=10.5240(2) Å, c=11.4659(2) Å, α=90°, β=93.5058° (7) and γ=90°.

In an embodiment of the present invention, a process for preparing a co-crystal of sulfentrazone and metribuzin by using any of the following methods:

i. mixing sulfentrazone and a triazinone herbicide in an aqueous condition followed by providing energy;

ii. solution crystallization
iii. dry grinding
iv. solvent drop grinding technique
v. melt crystallization In an embodiment of the present invention, the co-crystal of sulfentrazone and metribuzin herbicide can be obtained by any conventional processes known to the person skilled in the art used for preparing such co-crystals.

The present invention further provides a process for preparation of a co-crystal of sulfentrazone and a triazinone herbicide.

In an embodiment, the process for preparing a co-crystal of sulfentrazone and a triazinone herbicide wherein said co-crystal is obtained by solution crystallization or grinding or heating or solvent drop grinding or melt crystallization or mixing sulfentrazone and a triazinone herbicide in an aqueous condition.

In an embodiment of the present invention, a process for preparing a co-crystal of sulfentrazone and metribuzin by mixing sulfentrazone and metribuzin involve suspending sulfentrazone and metribuzin in water followed by providing energy sufficient to facilitate intermolecular interactions between sulfentrazone and metribuzin.

In an embodiment of the present invention, a process for preparing a co-crystal of sulfentrazone and metribuzin comprises mixing sulfentrazone and metribuzin in an aqueous condition followed by providing energy.

In an embodiment of the present invention, a process for preparing a co-crystal of sulfentrazone and metribuzin comprises preparing a solution of sulfentrazone and a triazinone herbicide using an organic solvent, water, or a mixture of water and an organic solvent and triturating or precipitating with an anti-solvent to obtain said co-crystal of sulfentrazone and a triazinone herbicide.

The solvent is selected from aliphatic alcohols, ketones, esters, ethers, polar protic solvents, polar aprotic solvents, halogenated solvents, aliphatic hydrocarbon or aromatic hydrocarbon and said anti-solvent is selected from aliphatic or aromatic hydrocarbon solvents.

In an embodiment the process for preparing a co-crystal of sulfentrazone and metribuzin comprises heating a mixture of sulfentrazone and a triazinone herbicide to melt to obtain said co-crystal of sulfentrazone and a triazinone herbicide.

In an embodiment of the present invention, the process for preparing a co-crystal of sulfentrazone and metribuzin by solution crystallization involve completely dissolving sulfentrazone and metribuzin in a suitable solvent, and further co-crystallization is induced by cooling or evaporation or precipitation.

In an embodiment the solvent can be selected from aliphatic alcohols, ketones, esters, ethers, polar protic solvents, polar aprotic solvents, halogenated solvents, aliphatic hydrocarbon, and aromatic hydrocarbon.

In an embodiment the solvent can be selected from methanol, ethanol, isopropyl alcohol, acetone, dichloromethane, dichloroethane, dichloropropane, trichloroethane, chloroform, and ethyl acetate.

In an embodiment of the present invention, co-crystallization induced by cooling involve, separately preparing the saturated solution of sulfentrazone and metribuzin at an elevated temperature. Afterwards, combining both the solutions at the same temperature and cooling down to 0° C. to 20° C., preferably to 3° C. to 8° C. (e.g. 5° C.). The so-formed co-crystals can be separated from the resulting suspension by conventional techniques (e.g. filtration).

In an embodiment of the present invention, co-crystallization induced by evaporation involve partial or complete removal of solvent by using commonly used evaporation techniques (e.g. heating or reduced pressure).

In an embodiment of the present invention, co-crystallization induced by precipitation involve complete dissolution of sulfentrazone and metribuzin in a suitable solvent The crystallization is induced by lowering the solubility of the solute by addition of a solvent, in which the solubility of the sulfentrazone and solubility of metribuzin is preferably lower than 10 g/l and in particular lower than 2 g/l at room temperature (herein below referred to as "anti-solvent"). A convenient suitable anti-solvent is a non-polar solvent, e.g. n-hexane, n-heptane, diethyl ether, petroleum ether, 1,4-dioxane, cyclohexanone, toluene or xylene.

In an embodiment of the present invention, a process for preparing a co-crystal of sulfentrazone and metribuzin by dry grinding involve combining sulfentrazone and metribuzin and subsequently applying shear forces.

In an embodiment of the present invention, dry grinding process for preparing a co-crystal of sulfentrazone and metribuzin by applying shear forces is preferably performed at a temperature of at least 15° C., frequently at a temperature of at least 20° C., preferably at a temperature of at least 30° C., in particular of at least 35° C., e.g. from 15° C. to 80° C.

In an embodiment of the present invention, a process for preparing a co-crystal of sulfentrazone and metribuzin by solvent drop grinding technique.

In an embodiment of the present invention, a process for preparing a co-crystal of sulfentrazone and metribuzin by solvent drop grinding technique involve organic solvent or a mixture of water and organic solvent where sulfentrazone and metribuzin have a comparable solubility.

More preference is given to organic solvents of the group 1, and to their mixtures with water. In the mixtures with water the relative amount of organic solvent and water may vary from 200:1 to 1:200 (v/v), in particular from 1:5 to 1:100 (v/v).

Suitable solvents are polar organic solvents as defined above.

An especially suitable organic solvent to be used alone or in mixture with water is an alcohol as mentioned above ($C_1$-$C_4$-alkanols such as methanol, ethanol, n-propanol or isopropanol).

The solvent drop grinding process can be simply performed by pouring solvent onto the mixture of sulfentrazone and metribuzin in a drop-wise manner and applying shear forces (e.g. with a rotor-stator mill).

The solvent drop grinding process is usually performed at a temperature of at least 5° C., preferably at least 10° C. and in particular at least 20° C., e.g. from 5 to 80° C., preferably from 10 to 55° C., in particular from 20 to 40° C.

The time required for formation of the co-crystal by the solvent drop grinding process depends on the temperature, the type of solvent and is generally 1 h. In any case, complete conversion is achieved after one week; however, the complete conversion will usually require not more than 24 h.

In an embodiment of the present invention, a process for preparing a co-crystal of sulfentrazone and metribuzin by melt crystallization involve heating of sulfentrazone and metribuzin mixture in a porcelain dish on a paraffin oil bath maintained at 200° C. Further, incubating molten mass in a vessel containing 25 ml water at 90° C. using water bath. The co-crystal thus obtained is dried at room temperature overnight and further analyzed for its characterization.

In an embodiment of the present invention, a process for preparing a co-crystal of sulfentrazone and metribuzin by mixing sulfentrazone and metribuzin in an aqueous condition followed by providing energy involve milling the mixture of sulfentrazone and metribuzin in an aqueous condition, optionally in presence of other agrochemical excipients and allowing the co-crystal formation by interaction in aqueous conditions. In an embodiment of the present invention, a process for preparing an agrochemical composition comprising co-crystal of sulfentrazone and metribuzin said process comprising:

a) pre-treatment to sulfentrazone and metribuzin to form a co-crystal;
b) admixing co-crystal of step (a) with agrochemical excipients as required to obtain mixture; and
c) further processing the resulting mixture of step (b) to obtain said composition In an embodiment of the present invention, pre-treatment comprises milling, grinding or providing suitable form of energy sufficient to allow the formation of co-crystal of sulfentrazone and metribuzin herbicide.

In an embodiment of the present invention, pre-treatment comprises heating the mixture of sulfentrazone and metribuzin herbicide and allowing the formation of co-crystal of sulfentrazone and triazinone herbicide.

In an embodiment of the present invention, pre-treatment comprises subjecting the mixture of sulfentrazone and metribuzin herbicide to amorphization by way of grinding, melting, milling or other suitable means and allowing the formation of co-crystal of sulfentrazone and triazinone herbicide.

In an embodiment of the present invention, co-crystal thus formed in step (b) is then allowed to mix with suitable agrochemical excipients to obtain mixture and processed further to obtain the agrochemical composition in a suitable form.

The preferred methods for performing step b) and step c) are described previously.

In an embodiment, there is provided a process for preparing an agrochemical composition of a co-crystal of sulfentrazone and a triazinone herbicide, said process comprising:

a) pre-treatment to sulfentrazone and a triazinone herbicide to form a co-crystal;
b) admixing co-crystal of step (a) with agrochemically acceptable excipients to obtain said composition.

According to another embodiment of the present invention, the process for preparing an agrochemical composition comprising:

a) pre-treatment to sulfentrazone and metribuzin by heating followed by cooling the mixture to room temperature to obtain co-crystal;
b) admixing co-crystal of step (a) with agrochemical excipients in presence of water to obtain homogeneous agrochemical composition.

Typically, the process for preparing an agrochemical composition comprising:

a) pre-treatment to sulfentrazone and metribuzin by heating at temperature in the range of about 70-80° C. for about 1 hour followed by cooling the mixture to room temperature to obtain co-crystal;
b) admixing co-crystal of step (a) with agrochemical excipients in presence of water under high shear and adding one or more dispersing agent and/or wetting agent to obtain slurry.
c) optionally milling the slurry to achieve particle size as per specification preferably $d_{10}\leq1$, $d_{50}\leq4$, $d_{90}\leq10$ and $d_{100}\leq35$ μm by maintain mill temperature at ≤25° C.
d) mixing the slurry for about 1 hour to get homogeneous agrochemical composition.

According to an embodiment of the present invention, the process for preparing an agrochemical composition comprising:

a) preparing an aqueous mixture of agrochemically suitable excipients to obtain a homogeneous solution.
b) adding metribuzin and sulfentrazone in the homogeneous solution of step (a) to obtain a slurry;
c) optionally milling the slurry.
d) heating the slurry of step (b) or (c) and cooling to room temperature.
e) optionally charging other agrochemical excipient to the slurry of step (d) and mixing to get homogeneous agrochemical composition.

According to an embodiment of the present invention, the process for preparing an agrochemical composition comprising:

a) preparing an aqueous solution of agrochemically suitable excipients, preferably an anionic and non-ionic dispersing agents a mixer under high shear to obtain a homogeneous solution.
b) adding metribuzin and sulfentrazone in the homogeneous solution of step (a) to obtain a slurry;
c) optionally milling the slurry to achieve particle size as per specification of $d_{10}\leq1$, $d_{50}\leq4$, $d_{90}\leq10$ and $d_{100}\leq35$ μm and maintaining the mill temperature at ≤25° C.
d) heating the slurry of step (b) or (c) at temperature range of 70 to 80° C., mixing for about 1 hour and cooling to room temperature;
e) charging other agrochemical excipient for example thickener gel to the slurry of step (b) or step (d) or and mixing to get homogeneous agrochemical composition.

The process comprises optionally following the step (c) after step (d) to achieve particle size specification of step (c);

The step (e) comprises preparing a thickener (2% solution) gel by charging a vessel with Proxel GXL and Rhodopol 23, mixing for 30 minutes and adding water and continue mixing for 1 hour.

In an embodiment of the present invention, steps in the process for preparing an agrochemical composition comprising co-crystal of sulfentrazone and metribuzin may not be fixed and can be in any order to achieve an agrochemical composition according to the present invention.

In an embodiment of the present invention, the agrochemical compositions of the present invention may be in a solid or liquid form.

According to preferred embodiment, the agrochemical compositions of the present invention is a liquid formulation.

According to an embodiment of the present invention, the liquid agrochemical composition may be formulated as suspension concentrate (SC), as an emulsion concentrate (EW), as an oil-based suspension concentrate (OD), and/or suspoemulsions (SE).

According to the preferred embodiment of the present invention, the liquid agrochemical composition is formulated as suspension concentrate (SC).

The present invention relates to process for preparing a liquid agrochemical composition comprising co-crystal of sulfentrazone and metribuzin said process comprising:

(a) pre-treatment to sulfentrazone and metribuzin to form a co-crystal;
(b) admixing co-crystal of step (a) with agrochemical excipients as required in an aqueous condition to obtain mixture; and (c) further processing the resulting mixture of step (b) to obtain said composition In an embodiment of the present invention, steps in the process for preparing a liquid agrochemical composition comprising co-crystal of sulfentrazone and metribuzin may not be fixed and can be in any order to achieve liquid agrochemical composition according to the present invention.

In another embodiment of the present invention, co-crystal of a liquid agrochemical composition is obtained by "pre-treatment" mean a process that allows sulfentrazone and a triazinone herbicide to form a co-crystal prior to its incorporation into the liquid agrochemical composition.

In an embodiment of the present invention, pre-treatment of sulfentrazone and metribuzin involve bringing together and milling, grinding or heating or providing suitable form of energy sufficient to allow the formation of co-crystal of sulfentrazone and metribuzin.

In one embodiment, slurry of agrochemical excipients was first prepared and milled and then sulfentrazone and metribuzin were added at an elevated temperature (54° C.-60° C.) and milled along with the slurry of agrochemical excipients. Then, further processing was carried by adding thickeners to make the suspension concentrate.

In another embodiment, slurry of agrochemical excipients was first prepared, then sulfentrazone and metribuzin were added at an elevated temperature (54° C.-60° C.) and then milled along with the slurry of agrochemical excipients. Further processing was carried by adding thickeners to make the suspension concentrate.

In another embodiment, sulfentrazone and metribuzin are mixed and grinded and then allowing to melt (125° C.-140° C.) by providing heat to obtain co-crystal. The co-crystal is then cooled and crushed under milling condition. Separately prepared slurry of agrochemical excipients is then added to the mixture and again taken for milling. Finally, further processing is carried by adding thickeners to make the suspension.

In another embodiment, sulfentrazone and metribuzin are mixed and grinded to obtain mixture. The mixture is heated dynamically (54° C.-70° C.) then separately prepared slurry of agrochemical excipients is added to the mixture and again taken for milling. Finally, further processing is carried by adding thickeners to make the suspension. The present invention provides a liquid agrochemical composition comprising;

(a) a co-crystal of sulfentrazone and triazinone herbicide;

(b) acrylate polymer; and (c) glycerol.

According to an embodiment of the present invention, liquid agrochemical composition comprises acrylate polymer.

According to an embodiment of the present invention, acrylate polymer is selected from the group comprising of polymers of methyl acrylate, methacrylates, ethyl acrylate, 2-chloroethyl vinyl ether, 2-ethylhexyl acrylate, hydroxyethyl methacrylate, butyl acrylate, butyl methacrylate, and trimethylolpropane triacrylate (TMPTA). Acrylic polymers include, but are not limited to, Modified styrene/maleic anhydride copolymer (Envi-Pol 871), PAPI 27 Polymeric MDI, polymethyl methacrylate, polyacrylates, polyacrylate salts such as sodium polyacrylate, poly(vinyl acetate) (PVAc), and polyacrylamide.

In an embodiment of the present invention, the liquid agrochemical composition may further comprise of urea.

According to an embodiment of the present invention, liquid agrochemical composition comprises from about 0.1% w/w to about 40% w/w, preferably from about 0.1% w/w to about 30% w/w acrylate polymer of the total weight of the liquid agrochemical composition.

According to preferred embodiment of the present invention, liquid agrochemical composition comprises from about 1% w/w to about 30% w/w, preferably from about 0.1% w/w to about 30% w/w glycerol of the total weight of the liquid agrochemical composition.

According to an embodiment of the present invention, the liquid agrochemical composition comprises of water.

According to an embodiment of the present invention, the liquid agrochemical composition comprises from about 0.1% to about 99% w/w, preferably from about 10% to about 70% w/w water of the total weight of the liquid agrochemical composition. In an embodiment of the present invention, the liquid agrochemical composition may further comprise agrochemical excipients selected from one or more anionic and non-ionic surfactants, antifreeze agent, wetting agents, fillers, surfactants, anticaking agents, pH-regulating agents, preservatives, biocides, antifoaming agents, colorants and other formulation aids.

Suitable anionic surfactants include polyacrylates, alkylbezenesulfonates (Example: TERWET 1004) such as dodecylbenzenesulfonates, for example calcium dodecylbenzensulfonate, ethoxylated and/or propoxylated di- or tri-styrylphenol phosphates, ethoxylated and/or propoxylated di- or tri-styrylphenol sulfates, phenyl sulfonates, alkynaphtalenesulphonates, ethoxylated and/or propoxylated alcohol phosphate esters, ethoxylated and/or propoxylated alkylaryl phosphate esters, taurates, suphosuccinates, and polycarboxylates, Sodium alkylnaphthalene sulfonate formalin condensate or modified styrene-maleic anhydride copolymer). Examples of the commercially available alkyl naphthalene sulfonate sodium formalin condensate include Morwet D425, TERSPERSE 2020, Agrosurf WG-2300 and the like. Examples of the commercially available modified styrene-maleic anhydride copolymer TERSPERSE 2612.

Suitable non-ionic surfactants include alkoxylated surfactants and block copolymer surfactants. Examples of useful alkoxylated surfactants for the invention include castor oil ethoxylate, tridecyl alcohol ethoxylate, nonyl phenol ethoxylate, octyl phenol ethoxylate, tristryl phenol ethoxylate, phosphate ester ethoxylate, tallow amine ethoxylate, cocoa amine ethoxylate, and oleyl amine ethoxylate.

Suitable antifreeze agents that can be added to the liquid agrochemical composition are liquid polyols, for example ethylene glycol and propylene glycol.

Suitable pH regulating agents can be citric acid or phosphoric acid.

Wetting agents that can be added to the liquid agrochemical composition of the present invention include, but are not limited to: polyarylalkoxylated phosphate esters and their potassium salts (e.g., Soprophor® FLK, Stepfac TSP PE-K. Other suitable wetting agents include sodium dioctylsulfosuccinates (e.g., Geropon® SDS, Aerosol® OT) and ethoxylated alcohols (e.g., Trideth-6; Rhodasurf® BC 610; Tersperse® 4894).

Optionally, about 0.1 wt % to about 5.0 wt % of antifoaming or defoamers are employed to stop any unwanted foam generated while manufacturing suspension concentrate composition of the present application. The preferred antifoaming agent is selected from the group consisting of silicone-based compounds, alcohols, glycol ethers, mineral spirits, acetylene diols, polysiloxanes, organosiloxanes, siloxane glycols, reaction products of silicon dioxide and organosiloxane polymer, polydimethylsiloxanes or polyalkylene glycols alone or in combination. Defoamers that are suitable include AGNIQUE DFM 111S; SAG-10; SAG-1000AP; SAG-1529; SAG-1538; SAG-1571; SAG-1572; SAG-1575; SAG-2001; SAG-220; SAG-290; SAG-30; SAG-30E; SAG-330; SAG-47; SAG-5440; SAG-7133 and SAG-770.

Examples of thickening agents based on anionic heteropolysaccharides from the xanthan gum group are inter alia the Rhodopol 23®, Rhodopol G®, Rhodopol 50 MD®, Rhodicare T®, Kelzan®, Kelzan S® and Satiaxane CX91®.

Preservatives used may be benzisothiazolinone (Proxel GXL) or phenols, 2-bromo-2-nitropropane-1,3-diol, also known as Bronopol (Bioban BP 30), 5-chloro-2-methyl-4-isothiazolin-3-one & 2 methyl-4-isothiazolin-3 one (Kathon CG/ICP), Glutaraldehyde (Ucarcide 50), Chloromethylisothiazolinone (CMIT)/Methylisothiazolinone (MIT) (Isocil Ultra 1.5), 2.2-dibromo-3-nitrilopropioamide (Reputain 20), Natamycin & Nisin, Bronopol/CMIT/MIT (Mergal 721K3).

Suitable colorants (for example in red, blue and green) are, preferably, pigments, which are sparingly soluble in water, and dyes, which are water-soluble. Examples are inorganic coloring agents (for example iron oxide, titanium oxide, and iron hexacyanoferrate) and organic coloring agents (for example alizarin, azo and phthalocyanin coloring agents).

According to an embodiment of the present invention, compositions of the present invention comprises co-crystal of sulfentrazone and metribuzin and one or more pesticides other than the two components of said co-crystal.

Pesticides may be selected from herbicides, fungicides, insecticides, nematicides, acaricides, plant growth regulators, and safeners.

Preferably the pesticide is an herbicide selected from isoxazolidinone herbicide, a urea herbicide, a triazine herbicide, a hydroxybenzonitrile herbicide, a thiocarbamate herbicide, a pyridazine herbicide, chloroacetanilide herbicides; benzothiazole herbicides; carbanilate herbicides, cyclohexene oxime herbicides; picolinic acid herbicides; pyridine herbicides; quinolinecarboxylic acid herbicides; chlorotriazine herbicides, aryloxyphenoxypropionic herbicides, oxadiazolone herbicides, phenylurea herbicides, sulfoanilide herbicides, triazolopyrimidine herbicides, amide herbicides, pyridazine herbicides, dinitroaniline herbicides or combinations thereof.

Preferably the pesticide is a fungicide selected from amide fungicides, acylamino acid fungicides, anilide fungicides, benzamide fungicides, sulfonamide fungicides, strobilurin fungicides, aromatic fungicides, benzimidazole fungicides, carbamate fungicides, carbanilate fungicides, conazole fungicides (imidazoles triazoles), copper fungicides, dithiocarbamate fungicides, imidazole fungicides, organophosphorus fungicides, oxazole fungicides, pyrazole fungicides, pyridine fungicides or combinations thereof.

Preferably the insecticide is selected from arsenical insecticides, botanical insecticides, carbamate insecticides, benzofuranyl methylcarbamate insecticides, dimethylcarbamate insecticides, insecticides, dinitrophenol insecticides, fluorine insecticides, formamidine insecticides, fumigant insecticides, inorganic insecticides, insect growth regulators, benzoylphenylurea chitin synthesis inhibitors, macrocyclic lactone insecticides, neonicotinoid insecticides, nereistoxin analogue insecticides, organochlorine insecticides, organophosphorus insecticides, organothiophosphate insecticides, heterocyclic organothiophosphate insecticides, phenyl organothiophosphate insecticides, phosphonate insecticides, phosphonothioate insecticides, phosphoramidate insecticides, phosphoramidothioate insecticides, phosphorodiamide insecticides, oxadiazine insecticides, oxadiazolone insecticides, phthalimide insecticides, physical insecticides, pyrazole insecticides, pyrethroid insecticides, pyrethroid ether insecticides, pyrimidinamine insecticides, pyrrole insecticides, quaternary ammonium insecticides, sulfoximine insecticides, tetramic acid insecticides, tetronic acid insecticides, thiazole insecticides, thiazolidine insecticides and thiourea insecticides.

Preferably the nematicide is selected from abamectin, carvacrol, benomyl, carbofuran, carbosulfan, cloethocarb, alanycarb, aldicarb, aldoxycarb, oxamyl, tirpate, carbon disulfide, cyanogen, 1,2-dichloropropane, 1,3-dichloropropene, dimethyl disulfide, methyl bromide, methyl iodide, sodium tetrathiocarbonate, diamidafos, fenamiphos, fosthietan, phosphamidon, cadusafos, chlorpyrifos, dichlofenthion, dimethoate, ethoprophos, fensulfothion, fosthiazate, heterophos isamidofos, isazofos, phorate, phosphocarb, terbufos, thionazin, triazophos, imicyafos, mecarphon, acetoprole, benclothiaz, chloropicrin, dazomet, DBCP, DCIP, fluazaindolizine, fluensulfone, furfural, metam, methyl isothiocyanate, tioxazafen, xylenols.

Preferably the safener is selected from benoxacor, BPCMS, cloquintocet, cyometrinil, cyprosulfamide, dichlormid, dicyclonon, dietholate, fenchlorazole, fenclorim, flurazole, fluxofenim, furilazole, isoxadifen, jiecaowan, jiecaoxi, mefenpyr, mephenate, metcamifen, naphthalic anhydride and oxabetrinil.

In an embodiment of the present invention, a liquid agrochemical composition comprising from about 10% to about 40% w/w co-crystal of sulfentrazone and metribuzin, from about 1% to about 20% acrylic polymer and from about 1% to about 20% glycerol of the total weight of the liquid agrochemical composition.

In an embodiment of the present invention, a liquid agrochemical composition comprising from about 10% to about 40% w/w co-crystal of sulfentrazone and metribuzin, from about 1% to about 20% acrylic polymer and from about 1% to about 20% glycerol of the total weight of the liquid agrochemical composition wherein said agrochemical composition is formulated as suspension concentrate.

In an embodiment of the present invention, a liquid agrochemical composition comprising from about 10% to about 40% w/w co-crystal of sulfentrazone and metribuzin, from about 1% to about 20% alkali swellable polyacrylate, from about 0.1% to about 30% glycerol and from about 10% to about 30% water of the total weight of the liquid agrochemical composition wherein said liquid agrochemical composition is formulated as suspension concentrate.

Compositions according to the present invention can also be prepared by tank-mixing the active ingredient with auxiliaries suitable for the formulation of these active ingredients or alternatively may be sold as a kit of parts containing actives and other ingredients that may be mixed prior to spraying.

According to an embodiment of the present invention a method of controlling weeds is provided wherein said method comprising applying to a plant, or its habitat, plant seed or soil, an effective amount of a composition comprising a co-crystal of sulfentrazone and a triazinone herbicide.

According to an embodiment of the present invention a method of controlling weeds is provided wherein said method comprising applying to a plant, or its habitat, plant seed or soil, an effective amount of a composition comprising a co-crystal of sulfentrazone and metribuzin.

The herbicidal composition of the present invention maybe used to target weeds among the crops such corn, rice, wheat, barley, rye, oat, *sorghum*, cotton, soybean, peanut, buckwheat, beet, rapeseed, sunflower, sugar cane, tobacco, etc.; vegetables: solanaceous vegetables such as eggplant, tomato, pimento, pepper, potato, etc., cucurbit vegetables such as cucumber, pumpkin, zucchini, water melon, melon, squash, etc., cruciferous vegetables such as radish, white turnip, horseradish, kohlrabi, Chinese cabbage, cabbage, leaf mustard, broccoli, cauliflower, etc., asteraceous vegetables such as burdock, crown daisy, artichoke, lettuce, etc, liliaceous vegetables such as green onion, onion, garlic, and asparagus, ammiaceous vegetables such as carrot, parsley, celery, parsnip, etc., chenopodiaceous vegetables such as spinach, Swiss chard, etc., lamiaceous vegetables such as *Perilla frutescens*, mint, basil, etc, strawberry, sweet potato, *Dioscorea japonica, colocasia*, etc., flowers, foliage plants, turf grasses, fruits: pome fruits such apple, pear, quince, etc, stone fleshy fruits such as peach, plum, nectarine, *Prunus* mume, cherry fruit, apricot, prune, etc., citrus fruits such as orange, lemon, rime, grapefruit, etc., nuts such as chestnuts, walnuts, hazelnuts, almond, pistachio, cashew nuts, macadamia nuts, etc. berries such as blueberry, cranberry, blackberry, raspberry, etc., vines, kaki fruit, olive, plum, banana, oil palm, coffee, date palm, coconuts, etc., trees other than fruit trees; tea, mulberry, flowering plant, trees such as ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Picea*, and *Taxus* cuspidate, etc.

Thus, in another aspect, the present invention provides a method of controlling weeds at a locus, the method comprising a co-crystal of sulfentrazone and metribuzin to the locus.

The target weeds may be selected fromUrticaceae weeds: *Urtica urens*, Polygonaceae weeds: *Polygonum convolvulus, Polygonum lapathifolium, Polygonum pensylvanicum, Polygonum persicaria, Polygonum longisetum, Polygonum aviculare, Polygonum arenastrum, Polygonum cuspidatum, Rumex japonicus, Rumex crispus, Rumex obtusifolius, Rumex acetosa*; Portulacaceae weeds: *Portulaca oleracea;*

Caryophyllaceae weeds: *Stellaria media, Cerastium holosteoides, Cerastium* glomeratum, Spergula *arvensis, Silene gallica*

Molluginaceae weeds: *Mollugo verticillata*; Chenopodiaceae weeds: *Chenopodium album, Chenopodium ambrosioides, Kochia scoparia, Salsola kali, Atriplex* spp.; Amaranthaceae weeds: *Amaranthus retroflexus, Amaranthus viridis, Amaranthus lividus, Amaranthus spinosus, Amaranthus hybridus, Amaranthus palmeri, Amaranthus rudis, Amaranthus patulus, Amaranthus tuberculatos, Amaranthus blitoides, Amaranthus deflexus, Amaranthus quitensis, Alternanthera philoxeroides, Alternanthera sessilis, Alternanthera tenella*; Papaveraceae weeds: *Papaver rhoeas, Argemone Mexicana*; Brassicaceae weeds: *Raphanus raphanistrum, Raphanus sativus, Sinapis arvensis, Capsella bursa-pastoris, Brassica juncea, Brassica campestris, Descurainia pinnata, Rorippa islandica, Rorippa sylvestris, Thlaspi arvense, Myagrum rugosum, Lepidium virginicum, Coronopus didymus; Dinebra* weeds: *Dinebra* Americana, *Dinebra aquatic, Dinebra aristidoides, Dinebra bromoides, Dinebra calycina, Dinebra caudata, Dinebra chinensis, Dinebra chloride, Dinebra chondrosioides, Dinebra coerulescens, Dinebra cristata, Dinebra curtipendula, Dinebra decipiens, Dinebra divaricate, Dinebra divaricatissima, Dinebra dura, Dinebra guineensis, Dinebra hirsute, Dinebra hirta, Dinebra juncifolia, Dinebra ligulata, Dinebra lima, Dinebra melicoides, Dinebra nealleyi, Dinebra neesii, Dinebra panicea, Dinebra panicoides, Dinebra pubescens, Dinebra repens, Dinebra scabra, Dinebra secunda, Dinebra simoniana, Dinebra southwoodii, Dinebra squarrosa, Dinebra srilankensis, Dinebra tuaensis, Dinebra verticillate, Dinebra retroflexa. Dinebra haareri, Dinebra marquisensis, Dinebra perrieri, Dinebra polycarpha, Dinebra somalensis* Capparaceae weeds: *Cleome affinis*; Fabaceae weeds: *Aeschynomene indica, Aeschynomene rudis, Sesbania exaltata, Cassia obtusifolia, Cassia occidentalis, Desmodium tortuosum, Desmodium adscendens, Trifolium repens, Pueraria lobata, Vicia angustifolia, Indigofera hirsuta, Indigofera truxillensis, Vigna sinensis*; Oxalidaceae weeds: *Oxalis corniculata, Oxalis strica, Oxalis oxyptera*; Geraniaceae weeds: *Geranium carolinense, Erodium cicutarium*; Euphorbiaceae weeds: *Euphorbia helioscopia, Euphorbia maculate, Euphorbia humistrata, Euphorbia esula, Euphorbia heterophylla, Euphorbia brasiliensis, Acalypha australis, Croton glandulosus, Croton lobatus, Phyllanthus corcovadensis, Ricinus communis*; Malvaceae weeds: *Abutilon theophrasti, Sida rhombiforia, Sida cordifolia, Sida spinosa, Sida glaziovii, Sida santaremnensis, Hibiscus trionum, Anoda cristata, Malvastrum coromandelianum* Sterculiaceae weeds: *Waltheria indica*; Violaceae weeds: *Viola arvensis, Viola tricolor*; Cucurbitaceae weeds: *Sicyos angulatus, Echinocystis lobata, Momordica charantia*; Lythraceae weeds: *Lythrum salicaria*; Apiaceae weeds: *Hydrocotyle sibthorpioides*; Sapindaceae weeds: *Cardiospermum halicacabum*; Primulaceae weeds: *Anagallis arvensis*; Asclepiadaceae weeds: *Asclepias syriaca, Ampelamus albidus*; Rubiaceae weeds: *Galium aparine, Galium spurium* var. echinospermon, *Spermacoce latifolia, Richardia brasiliensis, Borreria alata*; Convolvulaceae weeds: *Ipomoea nil, Ipomoea hederacea, Ipomoea purpurea, Ipomoea hederacea* var. integriuscula, *Ipomoea lacunosa, Ipomoea triloba, Ipomoea acuminata, Ipomoea hederifolia, Ipomoea coccinea, Ipomoea quamoclit, Ipomoea grandifolia, Ipomoea aristolochiafolia, Ipomoea cairica, Convolvulus arvensis, Calystegia hederacea, Calystegia japonica, Merremia hedeacea, Merremia aegyptia, Merremia cissoides, Jacquemontia tamnifolia*; Boraginaceae weeds: *Myosotis arvensis*; Lamiaceae weeds: *Lamium purpureum, Lamium amplexicaule, Leonotis nepetaefolia, Hyptis suaveolens, Hyptis lophanta, Leonurus sibiricus, Stachys arvensis*; Solanaceae weeds: *Datura stramonium, Solanum nigrum, Solanum americanum, Solanum ptycanthum, Solanum sarrachoides, Solanum rostratum, Solanum aculeatissimum, Solanum sisymbriifolium, Solanum carolinense, Physalis angulata, Physalis subglabrata, Nicandra physaloides*; Scrophulariaceae weeds: *Veronica hederaefolia, Veronica persica, Veronica arvensis*; Plantaginaceae weeds: *Plantago asiatica*; Asteraceae weeds: *Xanthium pensylvanicum, Xanthium occidentale, Helianthus annuus, Matricaria chamomilla, Matricaria perforata, Chrysanthemum segetum, Matricaria matricarioides, Artemisia princeps, Artemisia vulgaris, Artemisia verlotorum, solidago altissima, Taraxacum officinale, Galinsoga ciliata, Galinsoga parviflora, Senecio vulgaris, Senecio brasiliensis, Senecio grisebachii, Conyza bonariensis, Conyza canadensis, Ambrosia artemisiaefolia, Ambrosia trifida, Bidens pilosa, Bidens frondosa, Bidens subalternans, Cirsium arvense, Cirsium vulgare, Silybum marianum, Carduus nutans, Lactuca serriola, Sonchus oleraceus, Sonchus asper, Wedelia glauca, Melampodium perfoliatum, Emilia sonchifolia, Tagetes minuta, Blainvillea latifolia, Tridax procumbens, Porophyllum ruderale, Acanthospermum australe, Acanthospermum hispidum, Cardiospermum halicacabum, Ageratum conyzoides, Eupatorium perfoliatum, Eclipta alba, Erechtites hieracifolia, Gamochaeta spicata, Gnaphalium spicatum, Jaegeria hirta, Parthenium hysterophorus, Siegesbeckia orientalis, Soliva sessilis*; Liliaceae weeds: *Allium canadense, Allium*

*vineale*; Commelinaceae weeds: *Commelina communis, Commelina bengharensis, Commelina erecta*; Poaceae weeds: *Echinochloa crus-galli, Setaria viridis, Setaria faberi, Setaria glauca, Setaria geniculata, Digitaria ciliaris, Digitaria sanguinalis, Digitaria horizontalis, Digitaria insularis, Eleusine indica, Poa annua, Alospecurus aequalis, Alopecurus myosuroides, Avena fatua, Sorghum halepense, Sorghum vulgare, Agropyron repens, Lolium multiflorum, Lolium perenne, Lolium rigidum, Bromus secalinus, Bromus tectorum, Hordeum jubatum, Aegilops cylindrica, Phalaris arundinacea, Phalaris minor, Apera spica-venti, Panicum dichotomiflorum, Panicum texanum, Panicum maximum, Brachiaria platyphylla, Brachiaria ruziziensis, Brachiaria plantaginea, Brachiaria decumbens, Brachiaria brizantha, Brachiaria humidicola, Cenchrus echinatus, Cenchrus pauciflorus, Eriochloa villosa, Pennisetum setosum, Chloris gayana, Eragrostis pilosa, Rhynchelitrum repens, Dactyloctenium aegyptium, Ischaemum rugosum, Oryza sativa, Paspalum notatum, Paspalum maritimum, Pennisetum clandestinum, Pennisetum setosum, Rottboellia cochinchinensis*; Cyperaceae weeds: *Cyperus microiria, Cyperus iria, Cyperus odoratus, Cyperus rotundus, Cyperus esculentus, Kyllinga gracillima*, Equisetaceae weeds: *Equisetum arvense, Equisetum palustre*, Trianthema weeds and the like.

In preferred embodiment the composition of the present invention is applied in soybean crop and is effective against several broadleaved weeds and grassy weeds, viz. velvetleaf, redroot pigweed, common lambsquaters, tumble pigweed and giant foxtail. In an embodiment, composition may be applied in a tank mix or as a pre-mixed composition.

In an embodiment, composition of the present invention may be applied either pre- or post-emergent. In a preferred embodiment, the composition of the present invention may be used pre-emergent, and pre-plant. The advantage of the composition is surprisingly good residual effects, and quick burndown of the weeds when applied pre-plant or pre-emergent.

According to an embodiment of the present invention, methods of application of agrochemical compositions as well as the mixtures according to the present invention are not particularly limiting. It can be simultaneous application of either a pre-mix or tank mix of active ingredients with auxiliaries suitable for the formulation or it can be a sequential application of one after the other.

According to an embodiment of the present invention, use of agrochemical composition comprising co-crystal of sulfentrazone and a triazinone herbicide.

According to an embodiment of the present invention, use of agrochemical composition comprising co-crystal of sulfentrazone and metribuzin.

According to an embodiment of the present invention, use of liquid agrochemical composition comprising co-crystal of sulfentrazone and metribuzin.

According to an embodiment of the present invention, a kit is provided wherein kit comprises a co-crystal of sulfentrazone and a triazinone herbicide; and other agrochemical excipients.

According to an embodiment of the present invention, a kit is provided wherein kit comprises a co-crystal of sulfentrazone and triazinone herbicide.

According to an embodiment of the present invention, a kit comprising co-crystal of sulfentrazone and metribuzin.

The invention shall now be described with reference to the following specific examples. It should be noted that the examples appended below illustrate rather than limit the invention and that those skilled in the art will be able to design many alternative embodiments without departing from the scope of the present invention.

EXAMPLES

Example 1: Preparation of the Co-Crystal of Sulfentrazone and Metribuzin

For a 1:1 co-crystal of sulfentrazone and metribuzin, 193.5 g of sulfentrazone and 107 g of metribuzin were charged into a round bottom flask. To this mixture was added 150 ml of dichloroethane. The solution was stirred at 30° C. overnight, 1000 ml hexane was added and stirred to obtain solid which were filtered and dried under vacuum to get 268 g of crystals. HPLC analysis: metribuzin-33.48% (w/w) and sulfentrazone-65.31% (w/w) which corresponds to about 1:1 of metribuzin:sulfentrazone (mole:mole). (FIG. 1).

Spectroscopic Analysis of Co-Crystal

Figure 2:
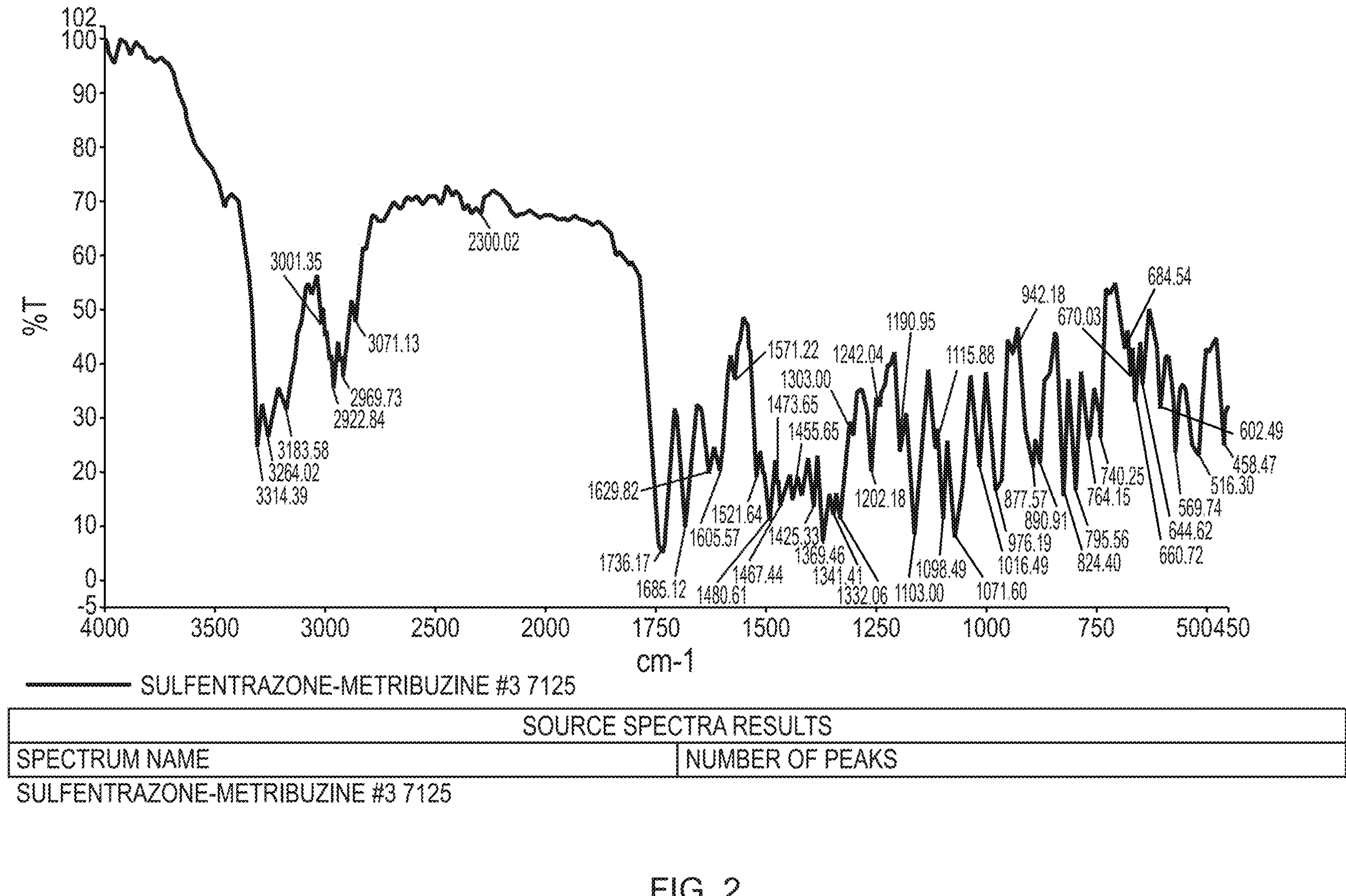
FIG. 2: Fourier Transform Infrared (FTIR) spectrum of co-crystal of sulfentrazone and metribuzin.

The co-crystal prepared according to Example-1 is further characterized by FT-IR (FIG. 2). The FT-IR spectrum of co-crystal of sulfentrazone and metribuzin is found to exhibit at least 3 characteristic values, particularly at least 5 characteristic values, or all the values selected from (±4 $cm^{-1}$) 3314, 3264, 2970, 1736, 1685, 1630, 1521, 1494, 1467, 1420, 1392, 1367, 1348, 1332, 1303, 1262, 1193, 1163, 1116, 1098, 1072, 976, 942, 893, 877, 824, 796, 764, 740, 670, 661, 645, 602, 570, 458, in particular from (±4 $cm^{-1}$) 3314, 3264, 1736, 1685, 1630, 1521, 1494, 1467, 1420, 1392, 1367, 1348, 1332, 1163, 1116, 1098, 1072, 976 and 824.

Crystallographic Analysis of the Co-Crystal

Figure 3:
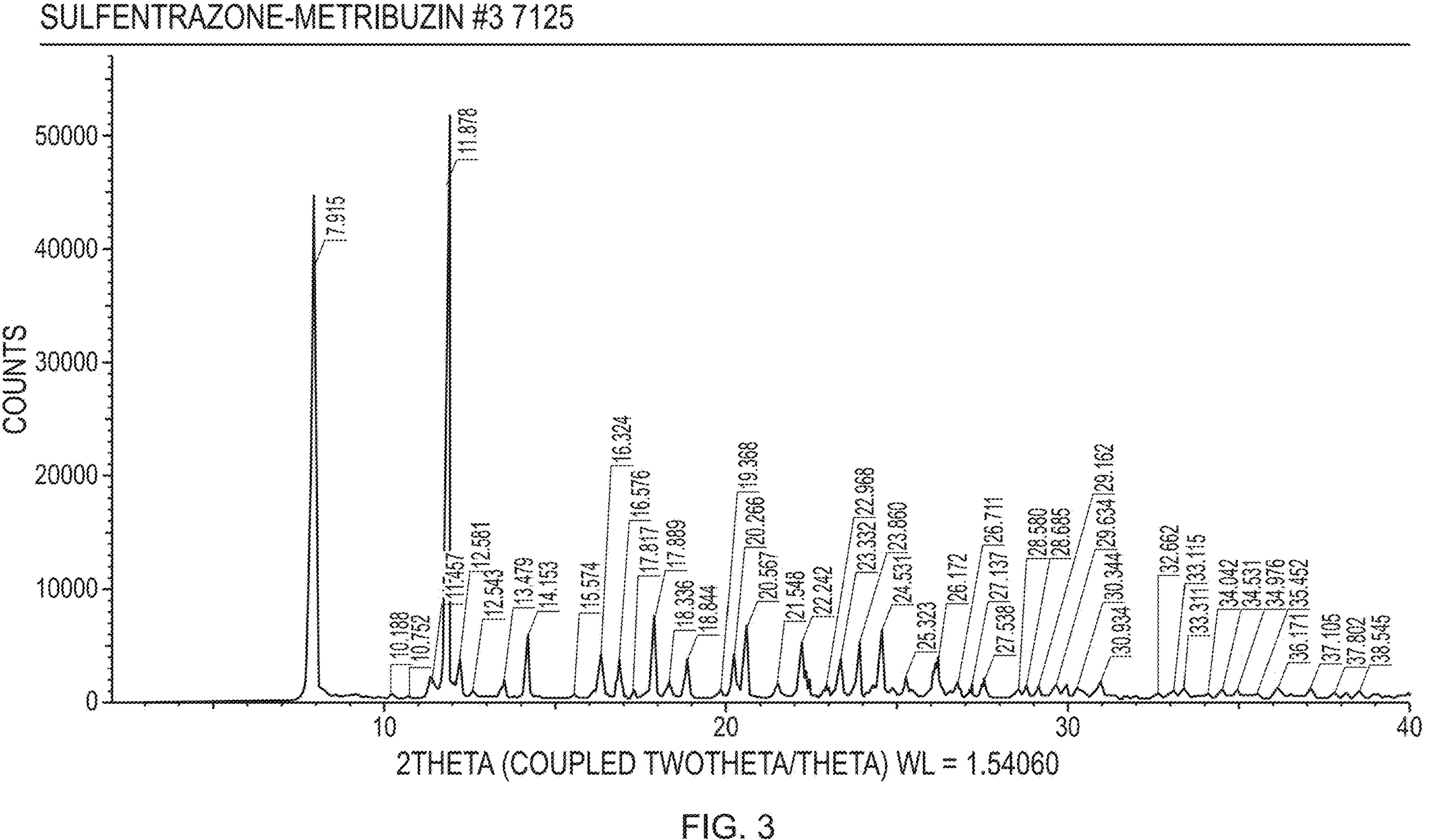
FIG. 3: Powder X Ray Diffraction (P-XRD) diffractogram of co-crystal of sulfentrazone and metribuzin.

The co-crystal prepared according to Example-1 is characterized by PXRD. (FIG. 3) The co-crystal of sulfentrazone and metribuzin shows an X-ray powder diffractogram at 25° C. (PXRD conditions: Instrument: Bruker make $2^{nd}$ generation D2 Phaser Powder X-Ray diffractometer; Operated at: 30.0 kV, 10 mA; Radiation: Cu-Kα; Wavelength: 1.54060° A, Scan Range: 2-40 2θ, Step size: 0.02°). The co-crystal of sulfentrazone and metribuzin shows at least 3, in particular at least 4 and more preferably all of the following reflexes, given in the following table 1 as 2θ values:

TABLE 1

PXRD of the co-crystal of Sulfentrazone and Metribuzin (Example-1) (25° C., Cu-Kα radiation, 1.54060 Å)

| 2θ values [°] | d[A°] |
|---|---|
| 7.9 ± 0.2 | 11.1 ± 0.2 |
| 11.8 ± 0.2 | 7.4 ± 0.2 |
| 12.1 ± 0.2 | 7.2 ± 0.2 |
| 14.1 ± 0.2 | 6.2 ± 0.2 |
| 17.9 ± 0.2 | 4.9 ± 0.2 |
| 20.5 ± 0.2 | 4.3 ± 0.2 |
| 22.2 ± 0.2 | 4.0 ± 0.2 |
| 23.3 ± 0.2 | 3.8 ± 0.2 |
| 24.5 ± 0.2 | 3.6 ± 0.2 |

Single Crystal X-Ray Diffraction

Figure 7:
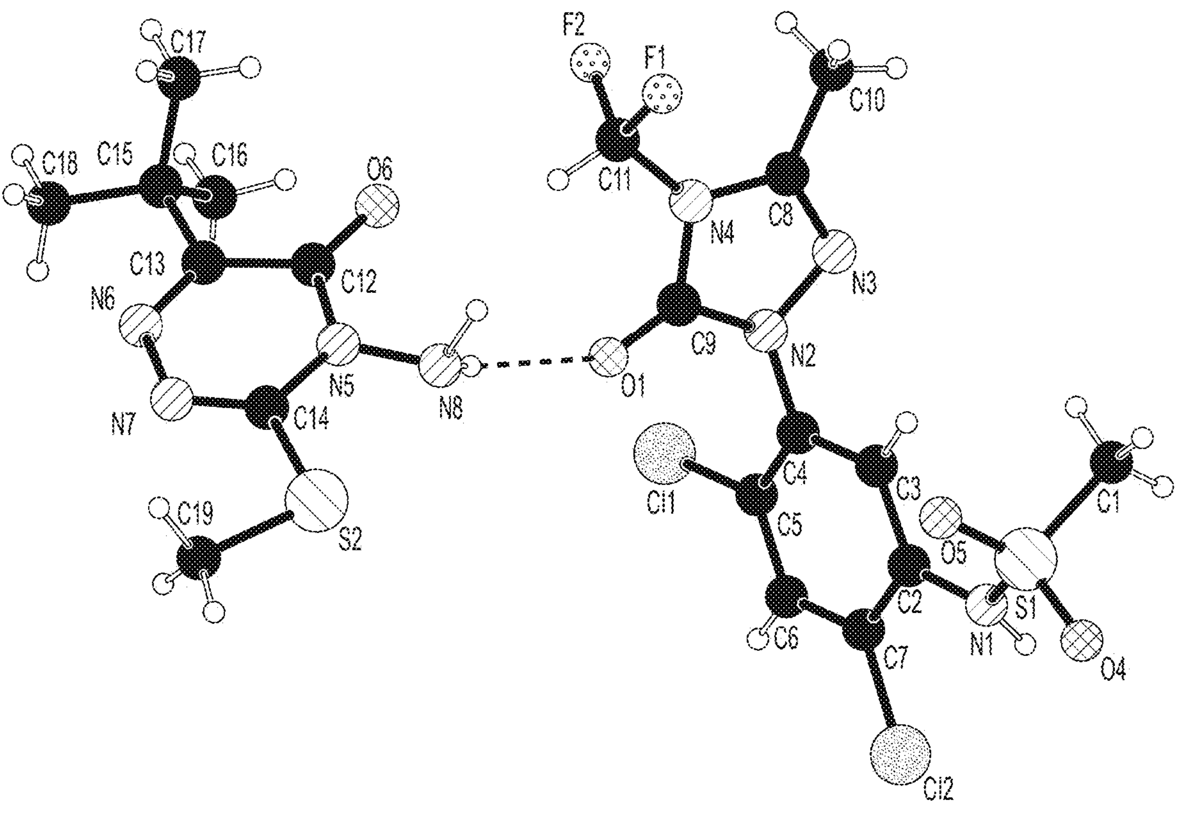
FIG. 7: Single crystal structure (in ball and stick model) of co-crystal of sulfentrazone and metribuzin.

Single crystal X-ray analysis determines the atomic and molecular structure of a co-crystal, including the molar relationship between the two compounds forming the co-crystal. The single crystal X-ray diffraction data of the co-crystal of sulfentrazone and metribuzin was collected on a Bruker D8 QUEST PHOTON-100 Detector. The structures were solved using direct methods, refined and expanded by Fourier techniques with SHELXTL-PLUS software package. Single crystal X-ray diffraction showing hydrogen bonding interaction forming co-crystal of sulfentrazone and metribuzin is given in FIG. 7.

Single crystal X-ray diffraction data and refinement for the co-crystal of sulfentrazone and metribuzin is given in the following table 2:

TABLE 2

| | |
|---|---|
| Empirical formula | $C_{19}H_{24}N_8O_4S_2Cl_2F_2$ |
| Formula weight | 601.49 gm/mol |
| Temperature | 294.15K |
| Wavelength | 0.71073 Å |
| Crystal system | Monoclinic |
| Space group | P $2_1$/c |
| Unit cell dimensions | a = 22.2825(4) Å α = 90°<br>b = 10.5240(2) Å β = 93.5058°(7)<br>c = 11.4659(2) Å γ = 90° |
| Volume | 2683.73 (8) $Å^3$ |
| Z | 4 |
| Density(calculated) | 1.4885 g/cc |
| Absorption coefficient | 0.454 $mm^{-1}$ |
| θ range for data collection | 5.26° to 50° |
| Reflections collected | 18592 |
| Independent reflections | 4631 [$R_{int}$ = 0.0306],<br>[$R_{sigma}$ = 0.0687] |
| Final R indices [I >= 2σ(I) | R1 = 0.0939, wR2 = 0.2592 |

Thermal Analysis of the Co-Crystal

DSC-measurement of the co-crystal was carried out on a Mettler-Toledo DSC 3 STARe system and STARe software was used to analyze the DSC data. A closed aluminum pan with 40 microliter capacity was used and the measurement was carried out under nitrogen flow with a heating rate of 10° C./min and a sample weight of 5 to mg.

Figure 4:
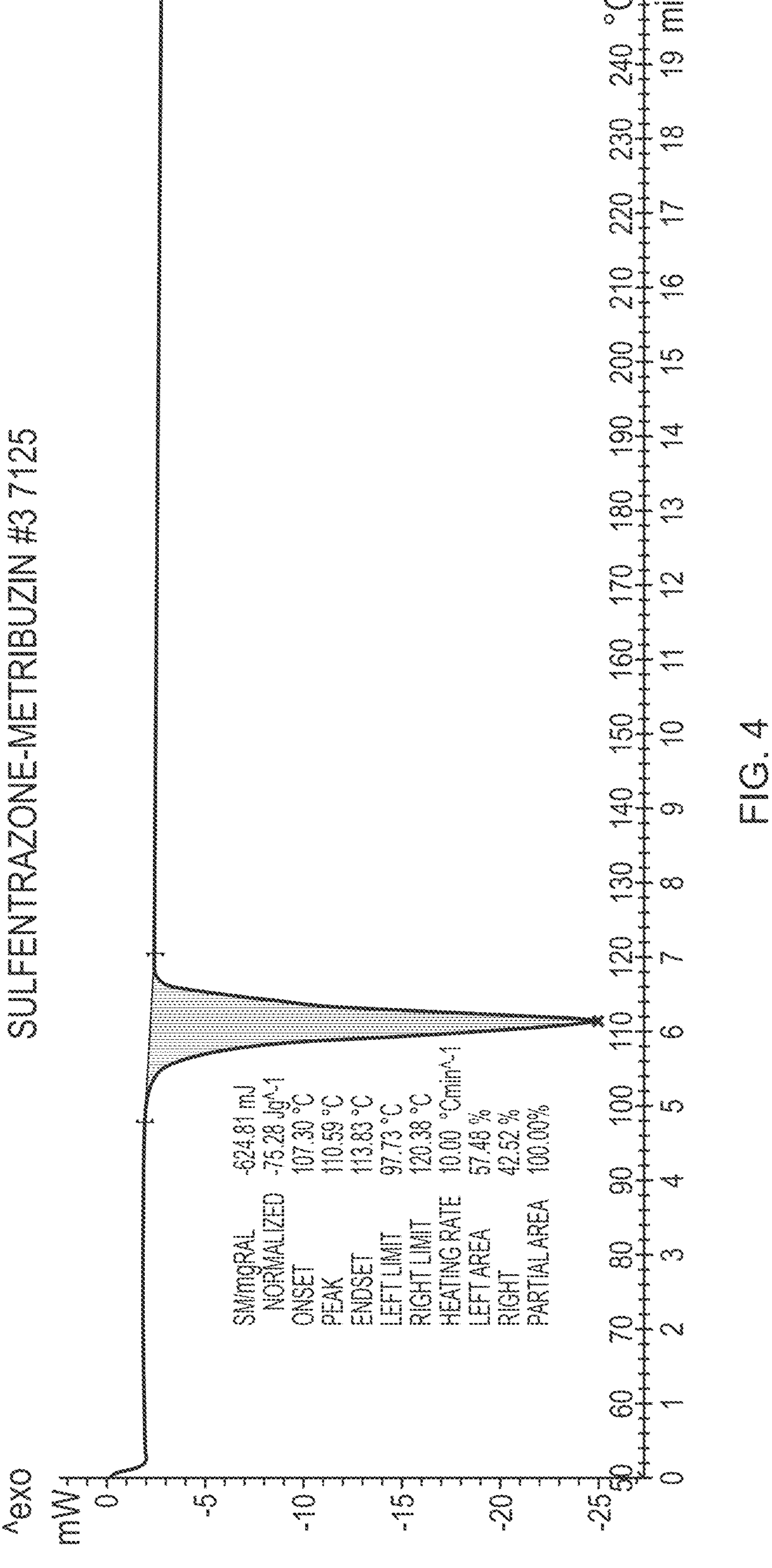
FIG. 4: Differential scanning calorimetry (DSC) thermogram of co-crystal of sulfentrazone and metribuzin.

DSC of the co-crystal exhibit an endothermic peak with onset at 107.3° C. and peak at 110.5° C. (FIG. 4) and specific heat of fusion (normalized) is between −69 Jg^−1 to −81 Jg^−1. The endothermic peak seen in DSC does not match with the individual melting points of sulfentrazone and metribuzin. Hence, analysis using DSC indicates co-crystallization.

Example 2: Suspension Concentrate (SC) Composition of Co-Crystal of Sulfentrazone and Metribuzin

| Ingredients | Quantity (% w/w) |
|---|---|
| Sulfentrazone-Metribuzin Co-crystal | 13.867 |
| Metribuzin | 22.43 |
| Propylene glycol | 5 |
| Polyalkylene glycol ether | 1 |
| Alkali swellable polyacrylate | 5 |
| Acrylic polymer | 2 |
| Silicone defoamer | 0.2 |
| Clay | 0.3 |
| Xanthan gum (2% gel) | 7.5 |
| 1,2-benzisothiazolin-3-one | 0.1 |
| Water | Q.S. |
| Total | 100 |

Figure 5:
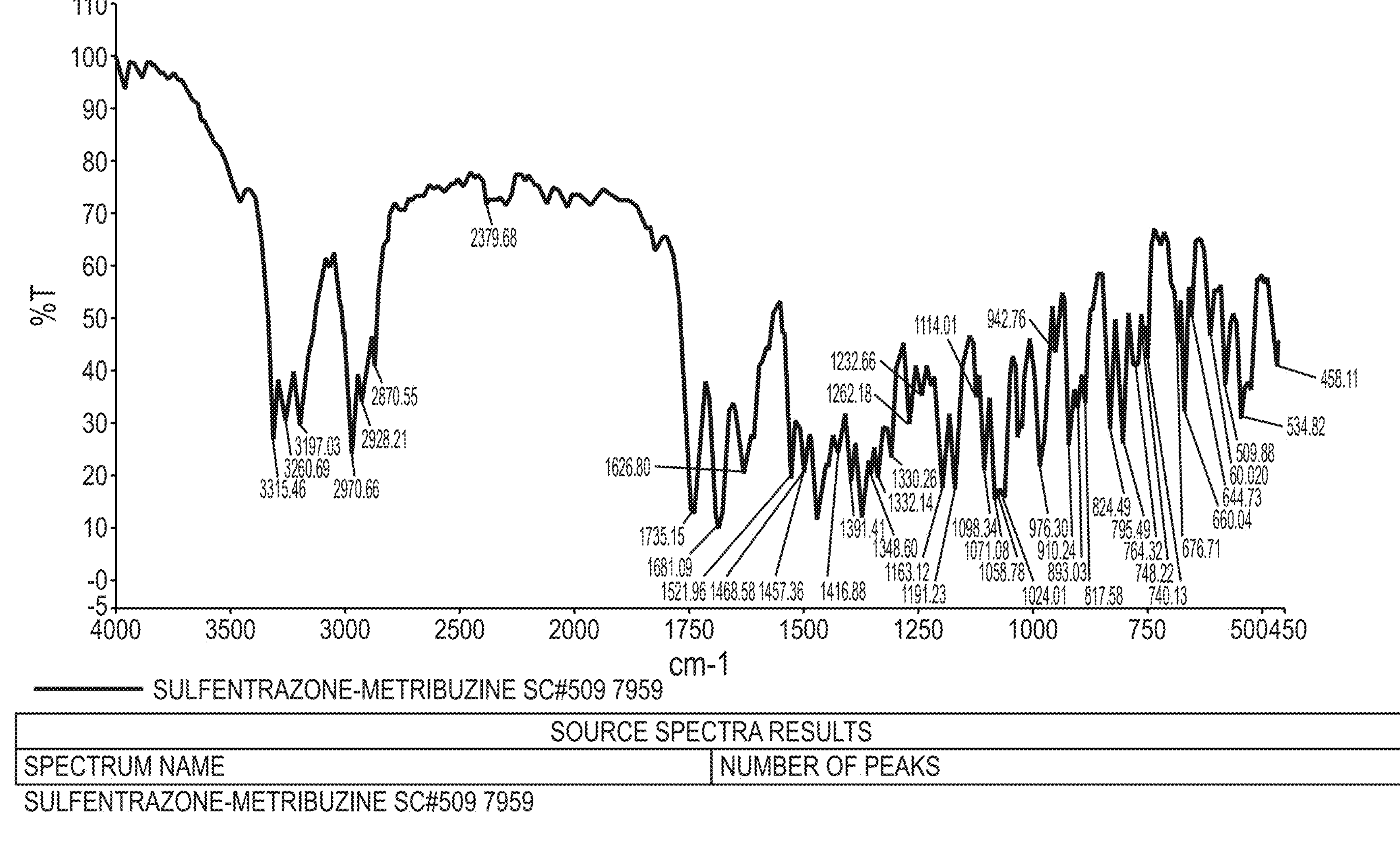
FIG. 5: FTIR spectrum of co-crystal of sulfentrazone and metribuzin in suspension concentrate.
Figure 6:
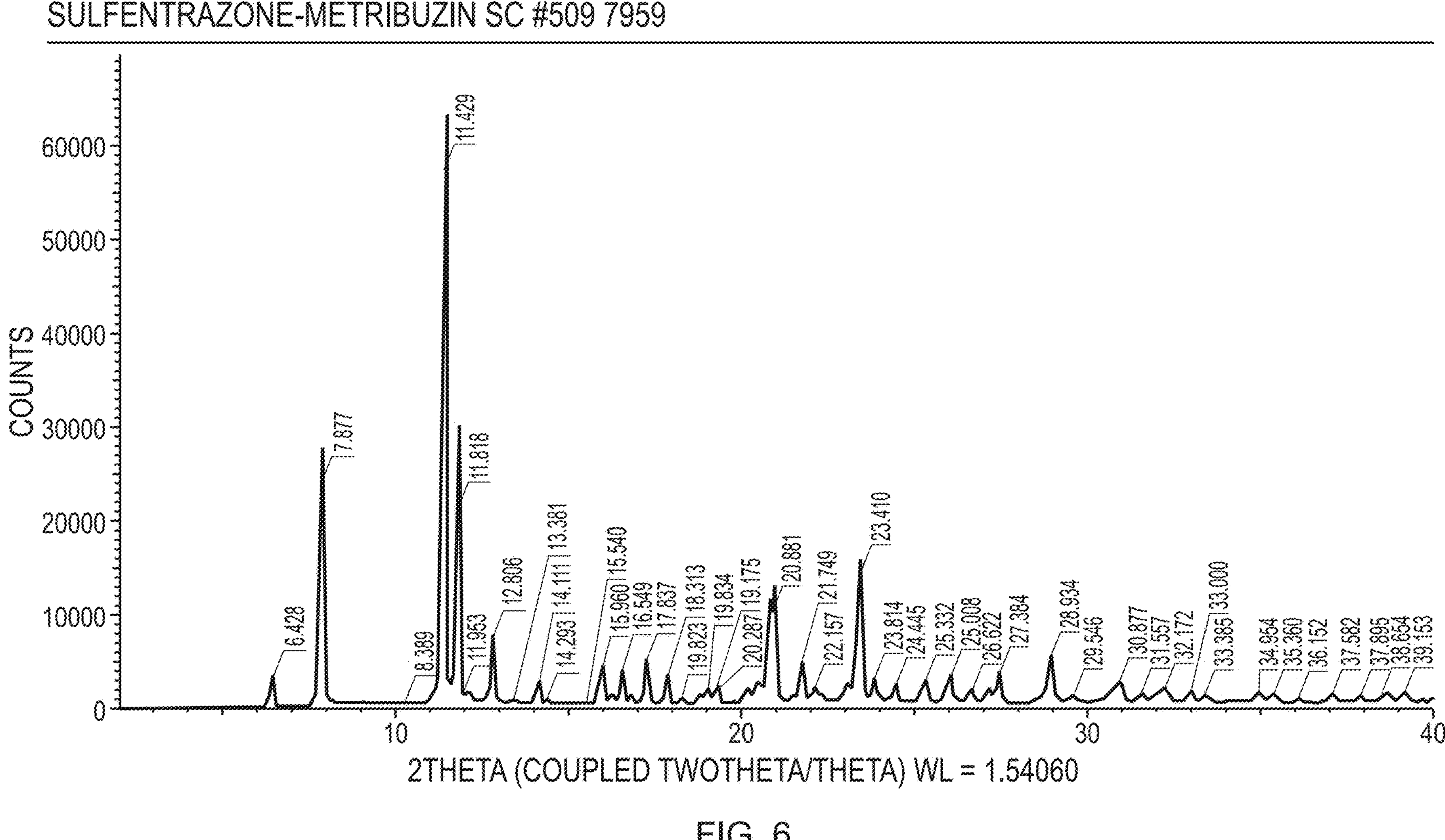
FIG. 6: P-XRD diffractogram of co-crystal of sulfentrazone and metribuzin in suspension concentrate.

5 g propylene glycol, 1 g polyalkylene glycol ether, 5 g alkali swellable polyacrylate, 2 g acrylic polymer was agitated with 42.60 g water for at least 1 hr. 0.2 g silicone defoamer was added to above stated mixture and subjected to agitation. 13.867 g of co-crystal of sulfentrazone and metribuzin and 22.43 g Metribuzin was added and subjected to homogenization for at least 1 hr followed by milling. 7.5 g of 2% Xanthan gum gel was added and the mixture was subjected to homogenization for at least 1 hr. The homogenized mixture was then set for uniform gelling. The composition obtained was then characterized by analytical techniques viz. FT-IR (FIG. 5) and P-XRD (FIG. 6).

Example 3:26.77% Sulfentrazone and 8.93% Metribuzin SC

| Ingredients | Quantity (w/w %) |
|---|---|
| Sulfentrazone (98% purity) | 9.1 |
| Metribuzin | 27.6 |
| Glycerin | 5 |
| Polyalkylene glycol ether | 1 |
| Alkali swellable polyacrylate | 4.7 |
| Acrylic polymer | 2.3 |
| Silicone defoamer | 0.2 |
| Clay | 0.3 |
| Xanthan gum | 0.15 |
| Water | Q.S. |
| Total | 100 |

27.85 g Metribuzin and 9.30 g Sulfentrazone technical were mixed to make homogeneous powder. The powder was then kept in incubator at 54° C. for 14 days to facilitate co-crystal formation. Separately, slurry was prepared in water by adding 5.0 g glycerin, 1.0 g polyalkylene glycol ether, 2.3 g acrylic polymer, 4.70 g alkali swellable polyacrylate, to the slurry preparation and stirred for 30 min to make the solution homogenous. Further, 0.2 g silicone defoamer and 0.3 g clay, were added one by one in sequence under continuous stirring. Homogeneous powder of Metribuzin and Sulfentrazone kept for pre-treatment was then charged under continuous stirring in the slurry obtained in the above step. The slurry was stirred for 30 min to break lumps and kept cooling down below 15° C. and was taken for bead milling. After slurry reaches the desired particle size (D90<10 micron) it was taken for Gellification. 2% aqueous gel obtained by adding 8 g xanthan gum and 0.2 g bronopol.

Example 4:26.77% Sulfentrazone and 8.93% Metribuzin SC

| Ingredient(s) | Quantity (% w/w) |
|---|---|
| Metribuzin Tech @ 97% | 27.85 |
| Sulfentrazone Tech @ 98% | 9.30 |
| Alkali swellable polyacrylate | 4.70 |
| Polyalkylene glycol ether | 1.00 |
| Acrylic polymer | 2.30 |
| 1,2-benzisothiazolin-3-one | 0.20 |
| Silicone defoamer | 0.20 |
| Clay | 0.30 |
| Glycerin | 5.00 |
| Xanthan gum | 8.00 |
| Water | Q.S. |
| Total | 100 |

Metribuzin and Sulfentrazone in above quantity were mixed to make homogeneous powder. The powder thus obtained was melted on oil bath at 105-110° C. after that it was allowed to cool at room temperature to obtain flakes. The flakes were then grinded to obtain a power. Separately, slurry was prepared in water by adding glycerin, polyalkylene glycol ether, acrylic polymer, alkali swellable polyacrylate, to the slurry preparation and stirred for 30 min to make the solution homogenous. Further, silicone defoamer, clay, and 1,2-benzisothiazolin-3-one are added one by one in sequence under continuous stirring. The powder of Metribuzin and Sulfentrazone obtained from pre-treatment was then charged under continuous stirring in the slurry obtained in the above step. The slurry was stirred for 30 min to break lumps and kept to cool down below 15° C. and was taken for bead milling. After slurry reaches the desired particle size (D90<10 micron) it was taken for Gellification. 2% aqueous gel obtained by adding 8 g xanthan gum and 1,2-benzisothiazolin-3-one.

Example 5: SC Composition of Sulfentrazone and Metribuzin

| Ingredients | Quantity (% w/w) |
|---|---|
| Sulfentrazone | 8.98 |
| Metribuzin | 27.22 |
| Propylene glycol | 5 |
| Polyalkylene glycol ether | 1 |
| Alkali swellable polyacrylate | 5 |
| Acrylic polymer | 2 |
| Silicone defoamer | 0.2 |
| 1,2-benzisothiazolin-3-one | 0.2 |
| Clay | 0.3 |
| Xanthan gum (2% gel) | 7.5 |
| Water | Q.S. |
| Total | 100 |

5 g propylene glycol, 1 g polyalkylene glycol ether, 5 g alkali swellable polyacrylate and 2 g acrylic polymer were agitated with 42.60 g water for at least 1 hr. 0.2 g silicone defoamer was added to above stated mixture and subjected to agitation. 8.98 g Sulfentrazone and 27.22 g Metribuzin were added and subjected to homogenization for at least 1 hr. followed by milling. 7.5 g of 2% Xanthan gum gel was added and the mixture was subjected to homogenization for at least 1 hr. The homogenized mixture was then set for uniform gelling.

Example 6: Sulfentrazone and Metribuzin SC

| Ingredient(s) | Quantity (% w/w) |
|---|---|
| Metribuzin Tech @ 97% | 27.85 |
| Sulfentrazone Tech @ 98% | 9.3 |
| Alkali swellable polyacrylate | 4.7 |
| Polyalkylene glycol ether | 1 |
| Acrylic polymer | 2.3 |
| 1,2-benzisothiazolin-3-one | 0.2 |
| Silicone defoamer | 0.2 |
| Clay | 0.3 |
| Glycerin | 5 |
| Xanthan gum | 8 |
| Water | Q.S. |
| Total | 100 |

Thermoregulatory vessel equipped with a high mixer was charge with partial water and stated to agitate. alkali swellable polyacrylate, acrylic polymer, polyalkylene glycol ether, silicone defoamer, partial amount of Glycerin and clay was added to obtain solution. The solution was then allowed to cool ≤25° C. Metribuzin and Sulfentrazone was added to the solution under high shear to obtain mixture. The mixture was then taken for milling (Particle size specification of $d_{10}$≤1, $d_{50}$≤4, $d_{90≤10}$ and $d_{100}$≤35 μm) at mill temperature at ≤25° C. to obtain milled base. The milled base was returned to mixing vessel heated to 54° C. and mixing carried for approximately 1 hour. Separately, thickener was prepared by charging a vessel with Glycerin, 1,2-benzisothiazolin-3-one, xanthan gum and water and mixed for 30 minutes. Thickener was added to mill base. The final composition was adjusted with water and released quality check and packaging.

Example 7: Sulfentrazone and Metribuzin SC

| Ingredients | Quantity (% w/w) |
|---|---|
| Sulfentrazone (98% purity) | 12.1 |
| Metribuzin | 24.6 |
| Glycerin | 5 |
| Polyalkylene glycol ether | 1 |
| Alkali swellable polyacrylate | 6 |
| Acrylic polymer | 3 |
| Xanthan gum (2% gel) | 7.5 |
| Clay | 0.15 |
| Water | Q. S. |
| Total | 100 |

Metribuzin, Sulfentrazone, Glycerin, polyalkylene glycol ether, alkali swellable polyacrylate, acrylic polymer, xanthan gum, clay and water were mixed in above quantity and processed as per the process given in Example-6 to obtain suspension concentrate composition of co-crystals comprising sulfentrazone and metribuzin.

Example 8: Sulfentrazone and Metribuzin SC

| Ingredients | Quantity (w/w %) |
|---|---|
| Sulfentrazone (98% purity | 9.1 |
| Metribuzin | 27.6 |
| Glycerin | 5 |
| Polyalkylene glycol ether | 1 |
| Alkali swellable polyacrylate | 6 |
| Acrylic polymer | 3 |
| Silicone defoamer | 0.2 |
| Clay | 0.3 |
| Xanthan gum | 0.15 |
| Water | Q. S. |
| Total | 100 |

Metribuzin, Sulfentrazone, Glycerin, Polyalkylene glycol ether, alkali swellable polyacrylate, acrylic polymer, silicone defoamer, xanthan gum, clay and water were mixed in above quantity and processed as per the process given in Example-6 to obtain suspension concentrate composition of co-crystals comprising sulfentrazone and metribuzin.

Example 9: Sulfentrazone and Metribuzin SC

| Ingredients | Quantity (w/w %) |
|---|---|
| Sulfentrazone | 9.17 |
| Metribuzin | 18.56 |
| Glycerin | 5 |
| Polyalkylene glycol ether | 1 |
| Alkali swellable polyacrylate | 6 |
| Acrylic polymer | 3 |
| Clay | 0.3 |
| Xanthan gum | 0.15 |
| Water | Q. S. |
| Total | 100 |

Process: Thermoregulatory vessel equipped with a high mixer was charged with partial water and stated to agitate. Alkali swellable polyacrylate, acrylic polymer, polyalkylene glycol ether, silicone defoamer, partial amount of Glycerin and clay were added to obtain a solution. The solution was then allowed to cool ≤25° C. Metribuzin and Sulfentrazone was added to the solution under high shear to obtain mixture. The material was milled to the required particle size and measure wet sieve retention according to in-process specification at temperature 25° C. or less than 25° C. during the milling process. Thickener was added to mill base. The final composition was adjusted with water and released quality check and packaging.

Example 10

Stability Study of Suspension Concentrate Composition

Stability features associated with the composition developed according to the present invention were studied. The compositions described in Example-3 and Example-4 were taken further to evaluate physicochemical parameters. It was found that the compositions of Example-3 and Example-4 remained stable when tested at ambient conditions i.e. room temperature and pressure. The compositions also passed 14 days and 28 days Accelerated Heat Stability (AHS) test and remained flowable suspension in off-white appearance. Amount of active content also been evaluated at all three stages (ambient, 14 days AHS and 28 days AHS). It was found that active content remained almost constant without any significant deterioration or loss. The composition also passed wet sieve testing as no crystals were observed to be retained on wet sieve. Particle size of composition was analysed and found to be nearly constant suggesting little/negligible particle size growth or crystal formation. (Table 3)

TABLE 3

| | Example 3 | | | Example 4 | | |
|---|---|---|---|---|---|---|
| Parameters | Ambient | 14 Days AHS at 54° C. | 28 Days AHS at 54° C. | Ambient | 14 Days AHS at 54° C. | 28 Days AHS at 54° C. |
| Description | Off white color suspension concentrate. | Complies | Complies | Off white color suspension concentrate. | Complies | Complies |
| Active content | 27.31 | 27.25 | 26.54 | 27.31 | 27.23 | 27.32 |
| Metribuzin (% w/w) | 9.13 | 9.11 | 8.87 | 9.07 | 9.12 | 9.19 |
| Sulfentrazone | | | | | | |
| pH of 1% Aq. Solution | 6.33 | 6.24 | 6.28 | 5.95 | 6.00 | 6.01 |
| Suspensibility (Gravimetric) % w/w | 93.7 | 91 | 90 | 96 | 93 | 91 |
| Wet sieve test material retains on75 micron (% w/w) | Nil | NIL | NIL | Nil | 0.3 | 0.5 |
| Particle size distribution (in micron) | D10 = 1.1<br>D50 = 2.8 | D10 = 2.8<br>D50 = 8.2 | | D10 = 1.0<br>D50 = 2.7 | D10 = 2.0<br>D50 = 6.2 | D10 = 2.2<br>D50 = 7.2 |
| Density @ 20° C. | 1.116 | — | — | | | |

Example 11

Bio-efficacy Data

The pre-emergence study was conducted on soyabean crop to test the efficacy of the agrochemical composition developed according to the present invention against several broadleaved weeds and grassy weeds, viz. velvetleaf, redroot pigweed, common lambsquaters, tumble pigweed and giant foxtail. The composition of Example-7 with co-crystal of sulfentrazone and metribuzin in 1:2 ratio was tested in soyabean field at the rate of 630 g a.i. The composition found to be effective on velvetleaf, redroot pigweed, common lambsquaters, tumble pigweed and giant foxtail at all intervals from 14DAA (14 days after application) to 35DAA (35 days after application). More than 60% control was observed for velvetleaf; 100% control of redroot pigweed was observed by the agrochemical composition of the present invention. Similarly, more than 90% control was observed for common lambsqauters and tumble pigweed. A good control of giant foxtail as also observed from 50-83% at 35DAA-21DAA observation as represented in below table.

TABLE 4

| Composition of Example-7 @630 g a.i. | | | | |
|---|---|---|---|---|
| | 14DAA | 21DAA | 28DAA | 35DAA |
| Velvetleaf % Control | 80 | 68 | 68 | 64 |
| Redroot Pigweed % Control | — | 100 | 100 | 100 |
| Common Lambsquaters % Control | — | 98 | 96 | 96 |
| Tumble Pigweed % Control | — | 100 | 100 | 99 |
| Giant Foxtail % Control | — | 83 | 78 | 50 |

Therefore, inventors of the present invention found that an agrochemical composition made of a co-crystal of sulfentrazone and a triazinone herbicide resulted into a stable composition. The formation of a co-crystal of sulfentrazone and triazinone herbicide, particularly metribuzin prior to the incorporation in the agrochemical composition imparted physical stability to the system. The acrylate polymer and glycerol in said agrochemical composition of co-crystal provided good performance over time, low or no sedimentation, and little particle size degradation. It is to be understood that the invention is not to be limited to the details of the above embodiments, which are described by way of example only.

The invention claimed is:

1. A co-crystal comprising sulfentrazone and metribuzin, wherein the co-crystal is characterized by a powder X-ray diffraction pattern comprising at least one peak at a diffraction angle of 2θ value of 7.8°, 11.8°, 14.1°, 17.8°, 22.1°, 23.4° and 24.4° (±0.2), and wherein the sulfentrazone and metribuzin are present in said co-crystal in a molar ratio of from 1:9 to 9:1.

2. The co-crystal as claimed in claim 1, wherein said sulfentrazone and metribuzin are present in a molar ratio from 2:1 to 1:2.

3. The co-crystal as claimed in claim 1, wherein said co-crystal is characterized by at least one of following: a DSC thermogram comprising an endothermic peak with an onset at 107.3° C. and a peak at 110.5° C.; or a single crystal X-ray diffraction having lattice parameters:

a=22.2825(4) A, b=10.5240(2) A, c=11.4659(2) A, a=90°, b=93.5058°(7) and g=90°.

4. A process for preparing the co-crystal of claim 1, comprising solution crystallization or grinding or heating or solvent drop grinding or melt crystallization or mixing sulfentrazone and metribuzin in an aqueous condition.

5. The process as claimed in claim 4, comprising preparing a solution of sulfentrazone and metribuzin using an organic solvent, water, or a mixture of water and an organic solvent, and triturating or precipitating with an anti-solvent to obtain said co-crystal of sulfentrazone and metribuzin.

6. The process as claimed in claim 5, wherein said solvent is selected from the group consisting of aliphatic alcohols, ketones, esters, ethers, polar protic solvents, polar aprotic solvents, halogenated solvents, aliphatic hydrocarbon, and aromatic hydrocarbons; and said anti-solvent is selected from the group consisting of aliphatic and aromatic hydrocarbon solvents.

7. The process as claimed in claim 4, wherein said process comprises heating a mixture of sulfentrazone and metribuzin to melt and obtain said co crystal of sulfentrazone and metribuzin.

8. An agrochemical composition comprising the co-crystal of claim 1.

9. The composition as claimed in claim 8, wherein said co-crystal comprises 10-90% of sulfentrazone and 90-10% of metribuzin by weight of the composition.

10. The composition as claimed in claim 8, wherein said composition is a liquid composition.

11. An agrochemical formulation comprising the composition of claim 8, in the form of a suspension concentrate.

12. A process for preparing an agrochemical composition comprising the co-crystal of claim 1, said process comprising: a) pre-treatment to sulfentrazone and metribuzin to form the co crystal; and b) admixing the co-crystal of step (a) with agrochemically acceptable excipients to obtain said composition.

13. The process as claimed in claim 12 wherein said agrochemical process comprises: a) pre-treatment to sulfentrazone and metribuzin by heating followed by cooling the mixture to room temperature to obtain the co-crystal; and b) admixing the co-crystal of step (a) with agrochemical excipients in presence of water to obtain a homogeneous agrochemical composition.

14. The process for preparing the agrochemical composition as claimed in claim 11, comprising a) preparing an aqueous mixture of agrochemically suitable excipients to obtain a homogeneous solution, b) adding metribuzin and sulfentrazone in the homogeneous solution of step (a) to obtain a slurry; c) optionally milling the slurry, d) heating the slurry of step (b) or (c) and cooling to room temperature, e) optionally charging other agrochemical excipient to the slurry of step (d), and mixing to provide a homogeneous agrochemical composition.

15. A method of controlling weeds comprising applying to a plant, or its habitat, plant seed or soil, a herbicidally effective amount of the co-crystal of claim 1.

* * * * *